United States Patent [19]
Rokhvarger et al.

[11] Patent Number: 5,911,941
[45] Date of Patent: Jun. 15, 1999

[54] PROCESS FOR THE PREPARATION OF THICK-WALLED CERAMIC PRODUCTS

[75] Inventors: Anatoly E. Rokhvarger, Brooklyn, N.Y.; Adam B. Khizh, Hackensack, N.J.

[73] Assignee: Nucon Systems, New York, N.Y.

[21] Appl. No.: 09/058,903

[22] Filed: Apr. 10, 1998

Related U.S. Application Data

[60] Provisional application No. 60/043,122, Apr. 10, 1997.

[51] Int. Cl.$^6$ .................................................... C04B 33/32
[52] U.S. Cl. ......................... 264/432; 264/434; 264/82; 264/606
[58] Field of Search .................. 264/432, 434, 264/82, 606

[56] References Cited

U.S. PATENT DOCUMENTS

| | | | |
|---|---|---|---|
| 3,585,258 | 6/1971 | Levinson . | |
| 3,704,523 | 12/1972 | Guerga et al. | 34/1 |
| 3,731,036 | 5/1973 | Hallier et al. | 219/10.55 |
| 4,045,639 | 8/1977 | Meisel | 219/10.55 |
| 4,057,702 | 11/1977 | Lacombe-Allard | 219/10.55 |
| 4,147,911 | 4/1979 | Nishitani | 219/10.55 |
| 4,292,262 | 9/1981 | Tobin, Jr. | 264/26 |
| 4,298,554 | 11/1981 | Vogel | 264/432 |
| 4,347,890 | 9/1982 | Ailin-Pyzik et al. | 164/528 |
| 4,505,787 | 3/1985 | Fuller et al. | 204/67 |
| 4,687,895 | 8/1987 | Chitre et al. | 219/10.55 |
| 4,771,153 | 9/1988 | Fukushima et al. | 219/10.55 |
| 4,880,578 | 11/1989 | Holcombe et al. | 264/26 |
| 4,963,709 | 10/1990 | Kimrey, Jr. | 219/10.55 |
| 5,010,220 | 4/1991 | Apte et al. | 219/10.55 |
| 5,072,087 | 12/1991 | Apte et al. | 219/10.55 |
| 5,077,268 | 12/1991 | Clark et al. | 505/1 |
| 5,108,670 | 4/1992 | Holcombe et al. | 264/26 |
| 5,122,633 | 6/1992 | Moshammer et al. | 219/10.55 |
| 5,164,130 | 11/1992 | Holcombe et al. | 264/26 |
| 5,202,541 | 4/1993 | Patterson et al. | 219/10.55 |
| 5,223,186 | 6/1993 | Eastman et al. | 264/25 |
| 5,227,600 | 7/1993 | Blake et al. | 219/10.55 |
| 5,252,267 | 10/1993 | Holcombe et al. | 264/26 |
| 5,266,762 | 11/1993 | Hoffman et al. | 219/10.55 |
| 5,294,763 | 3/1994 | Chamberlain et al. | 219/729 |
| 5,321,223 | 6/1994 | Kimrey, Jr. et al. | 219/745 |

(List continued on next page.)

FOREIGN PATENT DOCUMENTS 2296173  8/1994  United Kingdom .

OTHER PUBLICATIONS

Kirk–Othmer Encyclopedia of Chemical Technology; "Microwave Technology"; vol. 16; pp. 672–679, 694, 700 (No Date).

(List continued on next page.)

Primary Examiner—James Derrington
Attorney, Agent, or Firm—Milde, Hoffberg & Macklin, LLP

[57] ABSTRACT

A process for the preparation of ceramic articles having a thickness of at least about 2.5 cm, which comprises:

a) selecting the ceramic composition from the group consisting of silicate material, metal oxides, nitrides and carbides, and mixtures thereof, optionally adding ceramic fibers, such as boron nitride or silicon carbide fibers, to the ceramic composition, b) autoclaving the ceramic composition to increase its hydrogen form contents, which increases the composition's microwave absorptivity, c) forming the ceramic composition into the desired shape, and d) subjecting the composition so shaped to microwave energy to internally heat and thereby dry and sinter the composition, optionally with external heat applied by means of electrical resistance or gas fired heating. Novel apparatuses for the extrusion and vibrocompaction of ceramic compositions, the drying of ceramic masses, kilns for microwave-assisted firing of the ceramic articles, cars, and a hydraulic air handling system for tunnel kilns.

47 Claims, 6 Drawing Sheets

U.S. PATENT DOCUMENTS

| | | | |
|---|---|---|---|
| 5,365,042 | 11/1994 | Benoit et al. | 219/686 |
| 5,408,074 | 4/1995 | Warmbier et al. | 219/701 |
| 5,410,135 | 4/1995 | Pollart et al. | 219/730 |
| 5,432,325 | 7/1995 | Katz et al. | 219/759 |
| 5,466,917 | 11/1995 | Matsuki et al. | 219/730 |
| 5,507,986 | 4/1996 | Pak et al. | 264/62 |
| 5,521,360 | 5/1996 | Johnson et al. | 219/709 |
| 5,538,681 | 7/1996 | Wu | 264/432 |

OTHER PUBLICATIONS

Kirk–Othmer Encyclopedia of Chemical Technology; "Ceramics"; vol. 5; pp. 599–639 (No Date).

Richard L Lehman; "Overview of Ceramic Design and Process Engineering"; ASM International; (No Date).

FCR Wroe; "Scaling Up the Microwave Firing of Ceramics"; Microwaves II; pp. 449–465 (No Date).

Willard H. Sutton; "Microwave Processing of Ceramic Materials"; Ceramic Bulletin vol. 68 No. 2 1989; pp. 376–385, 1989.

I Ahmad, R. Dalton, and D. Clark; "Unique Application of Microwave Energy to the Processing of Ceramic Materials"; Journal of Microwave Power & Electromagnetic Energy; vol. 26 No. 3, 1991, pp. 128–138, 1991.

Keith Wilfinger; "Ceramic Package Fabrication for YMP Nuclear Waste Disposal"; Lawrence Livermore Natl Lab; pp. 1–32, Aug. 1994.

Kurte Slekafus; "The Remarkable Radiation Resistance of the Oxide Spinel"; Los Alamos Natl Lab; Sep. 1995.

Internet Printout of "The Mineral Spinel" (No Date).

Internet Printout of "Microwave Processing Group" (No Date).

Internet Printout of "Variable Frequency Microwave Furnace System" (No Date).

Internet Printout of "Ceramics & Ceramic Composites" 1995.

Internet Printout of "Microwave Processing of Ceramics" 1995.

Internet Printout of "5th Microwave and HF Conference" (No Date).

Internet Printout of "A Leader in the Design and Manufacture of Microwave and RF Filters" (No Date).

Internet Printout of "Energy Efficiency and Renewable Energy Program" (No Date).

Internet Printout of "Microwave Furnace Development" (No Date).

Internet Printout of "How Things Work—Microwave Ovens" (No Date).

Internet Printout of "Microwave Firing Equipment" (No Date).

Internet Printout of "Microwave Chemistry" (No Date).

Internet Printout of "Microwave Induced Combustion Synthesis of Ceramic and Ceramic–Metal Composites" Apr. 1995.

Internet Search Printout of "Synonyms of Minerals" (No Date).

American Ceramic Society Bulletin, vol. 75, No. 9, Sep. 1996, p. 34.

Internet Printout of "KCM White Fused Mullite" (No Date).

Internet Printout of "First Single–Crystal Mullite Fibers" (No Date).

Internet Printout of "Glaze & Clay Tutorial–2" (No Date).

Internet Printout of "Ceramics and Ceramic Composites" (No Date).

Internet Printout of "Chemical Preparation Methods for Ceramic Powders" (No Date).

Internet Printout of "KCM 73 Sintered Mullite" (No Date).

Internet Printout of "Microwave Processing of Ceramics" (No Date).

Internet Printout of "AEE–Mullite 3AL2O3" (No Date).

Internet Printout of "2.6 Production of SiC Fibre Toughened Glass and Glass–Ceramic Matrix Composites" (No Date).

Internet Printout of "AEE–Magnesium Aluminate, Spinel MgAl2O4 142" (No Date).

Internet Printout of "Equation of State of MgAl–2O–4–Spinel" No Date.

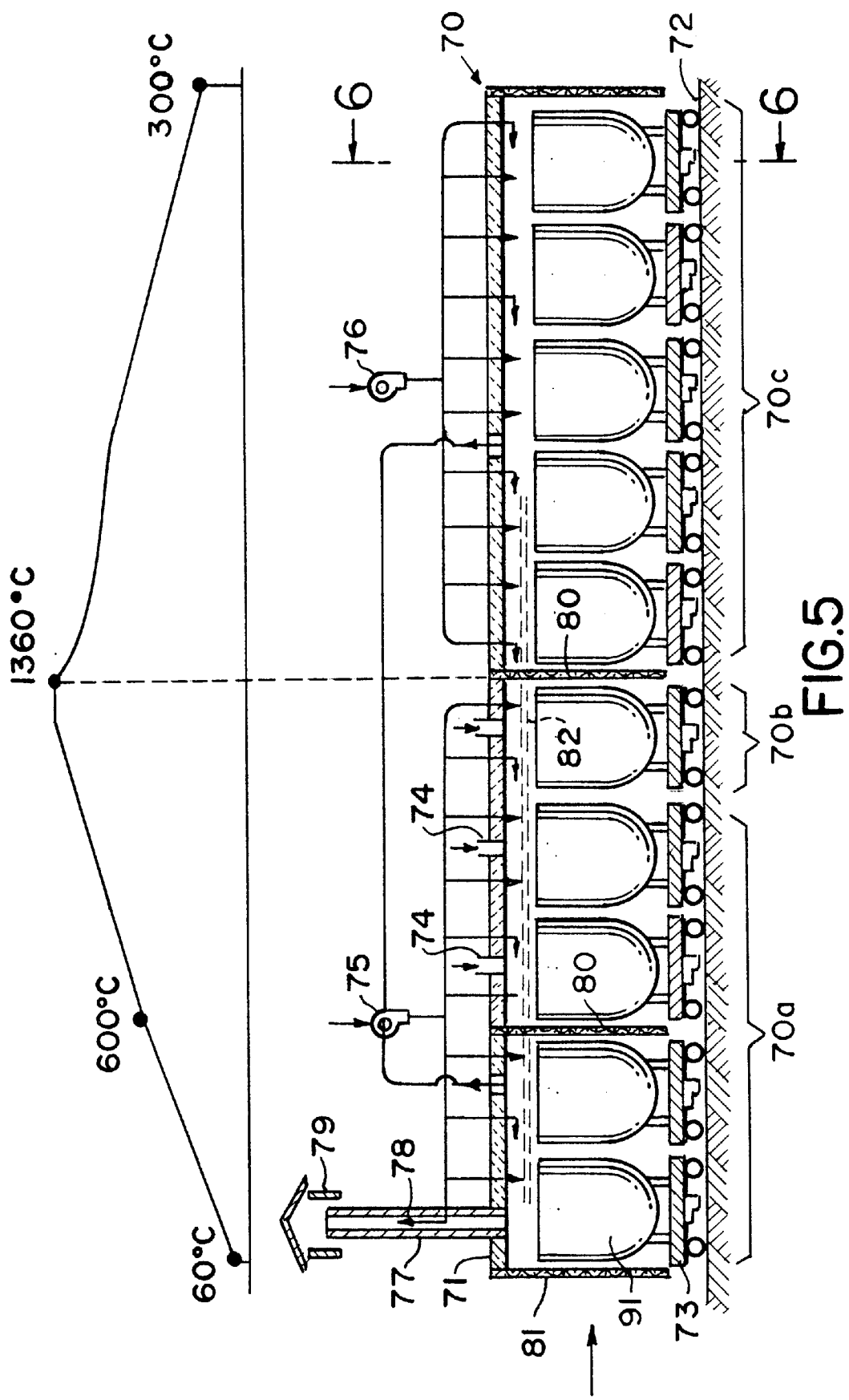

PROCESS FOR THE PREPARATION OF THICK-WALLED CERAMIC PRODUCTS

This application claims the benefit of U.S. Provisional application Ser. No. 60/043,122, filed Apr. 10, 1997.

BACKGROUND OF THE INVENTION

The present invention relates to a novel microwave-assisted process for the preparation of ceramic products, preferably large-sized, thick-walled ceramic products. The process is particularly suited for the preparation of large sized, thick-walled ceramic containers for the transport, storage, long-term containment and environmental isolation of nuclear and other hazardous waste.

There are currently 109 nuclear reactors in operation in the United States alone, with a further 424 worldwide. The average nuclear power plant produces about 20 metric tons of spent fuel each year. Current estimates are that the United States already has 28,000 metric tons of spent fuel stored. This number is expected to rise to 48,000 metric tons by 2003 and to 87,000 metric tons by 2030. These numbers do not reflect any waste from military nuclear applications. The safe and cost-effective disposal of this nuclear waste has created critical problems for the nuclear energy industry, for governments world wide and for the life, health and safety of humanity.

The process of the invention can produce ceramic containers that overcome the technical limitations and high cost of metal dry cask encapsulation or using glass or ceramic immobilization techniques, which are currently used.

In addition to ceramic containers for nuclear waste, the process of the invention is also applicable for producing any large size, thick-walled product that may be desired. For example, it may be used to produce high voltage electrical insulators, food and chemical apparatuses, engine blocks, very large slabs of ceramics that may be used to provide an exterior curtain wall on buildings; or roof tiles, large tiles for interior walls and floors; or structures either in one piece or a minimum number of pieces that combine floor, walls and ceiling for bathrooms, kitchens and other sanitary facilities. With large-sized ceramic plates that can be produced by the process of the invention, it is possible to substantially reduce the amount of skilled masonry work and tilesetting labor required to cover surfaces. This is desirable also in view of the declining skills of tilesetters. With large-sized plates, it is possible to minimize the number of joints that require grouting. With less grouting, there is less need for scrupulous cleaning to avoid mildew build-up over time and use, in the porous grout between the ceramic tiles. This is of particular benefit in hospitals—particularly in operating rooms—and other areas that must be maintained in a microbe-free state—such as food processing and pharmaceutical plants. The process of the invention is also useful in producing at less cost conventional ceramic products, such as sanitary ware.

Thousands of years ago man developed a ceramic technology for the conversion of a clay mass into stone-like shaped products with thin walls and moderate size at most.

Ceramic sewage and drainage pipes have been produced from ordinary clay for about two hundred years. Those pipes have a length up to 2,500 mm. Sewage pipes also may have an inner diameter up to 1,100 mm as described in ASTM, Designation: C 1208M-94, "Standard Specification for Vitrified Clay Pipe and Joints for Use in Jacking, Sliplining, and in Tunnels".

Vitrified clay pipes should be non-permeable for water solutions and be resistant and reliable for use in all possible combinations of aggressive organic and non-organic chemical hazards. However, these pipes are manufactured by conventional firing from conventional fire clay, shale, surface clay, or a combination of these materials. The firing of such large ceramic products requires long firing times with slow ramp up and down of temperature and considerable cost in conventional energy forms and consequential adverse effects on the environment.

Ceramics have low thermal conductivity. Therefore, the speed of conventional ceramic processing or an increase in the temperature of the external heating is inversely related to the body volume of the ceramic product. The greater the body volume, the lower the rise in temperature per unit of time and the longer the firing process. Consequently there is lower energy efficiency and, correspondingly, higher processing cost. The use of conventional heating methods in the production of large ceramic items requires a considerable amount of time and money to decrease body thermal gradients during a very long firing process.

The theory of microwave ceramic processing has not been fully developed. Some patents have issued on the use of microwaves in ceramic processing, however. Illustrative of such patents may be mentioned the following:

U.S. Pat. No. 3,585,258, granted Jun. 15, 1971, describes a method of firing a ceramic article by microwave energy at a firing temperature higher than available from the exposure of the article to the microwave energy which comprises locating the article in such a position as to subject it to the microwave energy, locating a plurality of loose or divided particles of a lossy material selected from the group consisting essentially of ferrites, iron, iron ore, and carbon in a predetermined fixed relationship with the article, which on exposure to microwave energy, provides the required firing temperature to fire the article, emitting microwave energy to the lossy material to generate a multitude of arcs therethrough, thereby generating high refractory heat energy for firing the article.

U.S. Pat. No. 4,147,911, granted Apr. 3, 1979, describes a method for sintering refractories which comprises mixing a group of dielectric refractory particles with 0.1 to 5% by weight of an electric conductor, in which the particle size of the electric conductor is not more than 10 times the skin depth of the conductor in the microwave region, forming the mixture and sintering the formed mixture thus obtained by means of microwave induction heating in a space surrounded by a metal wall.

In U.S. Pat. No. 4,687,895, granted Aug. 18, 1987, a system for heating objects serially within a plurality of separate heating zones is described. Objects are placed on pallets and sequentially moved through the plurality of heating zones. In a preferred embodiment, the pallets are fabricated of a microwave absorptive material and sequentially moved through a plurality of microwave cavities. The microwave cavities are provided with a source of microwave energy which heats the pallets, and by conduction, the objects placed thereon.

U.S. Pat. No. 4,771,153, granted Sep. 13, 1988, describes an apparatus for heating a ceramic by microwave power. The apparatus has a cavity resonator in which the ceramic is placed. The resonator is provided with a variable iris. The apparatus detects the temperature of the ceramic or other state of the ceramic, and adjusts the area of the opening in the iris in the resonator and the resonant frequency of the resonator according to a signal produced by the detection, in order to bring the resonator substantially into resonance and the degree of coupling to exactly or nearly unity.

Alternatively, the apparatus adjusts its microwave power for these purposes.

U.S. Pat. No. 4,880,578, granted Nov. 14, 1989, discloses a method for microwave sintering of materials, primarily metal oxides. Metal oxides that do not normally absorb microwave radiation at temperatures ranging from about room temperature to several hundred degrees centigrade are sintered with microwave radiation without the use of the heretofore required sintering aids. This sintering is achieved by enclosing a compact of the oxide material in a housing or capsule formed of an oxide which has microwave coupling properties at room temperature up to at least the microwave coupling temperature of the oxide material forming the compact. The heating of the housing effects the initial heating of the oxide material forming the compact by heat transference and then functions as a thermal insulator for the encased oxide material after the oxide material reaches a sufficient temperature to adequately absorb or couple with microwave radiation for heating thereof to sintering temperature.

In U.S. Pat. No. 4,963,709, granted Oct. 16, 1990, a microwave sintering system and method are provided for sintering of large and/or irregular shaped ceramic articles at microwave frequencies of at least 28 GHz in the hundreds of kilowatts power range in an untuned cavity. A 28 GHz, 200 kW gyrotron with variable power output is used as the microwave source connected to an untuned microwave cavity formed of an electrically conductive housing through an overmoded waveguide arrangement which acts in conjunction with a mode promoter within the cavity to achieve unexpected field uniformity. The part to be sintered is placed in the cavity and supported on a removable high temperature table in a central location within the cavity. The part is surrounded by a microwave transparent bulk insulating material to reduce thermal heat loss at the part surfaces and maintain more uniform temperature. The cavity may be operated at a high vacuum to aid in preventing arcing. The system reportedly allows controlled increased heating rates to provide rapid heating of a ceramic part to a selected sintering temperature where it is maintained by regulating the microwave power applied to the part.

U.S. Pat. No. 5,010,220, granted Apr. 23, 1991, discloses a process and apparatus for heating bodies to high temperatures at high pressures. The process involves locating the body in a chamber capable of acting as a resonant cavity for microwave radiation of a predetermined frequency. The body is then irradiated in the cavity with microwave energy of the predetermined frequency for a time sufficient to raise the temperature of the body to a suitable high temperature. Then, either subsequently or simultaneously, a fluid at high pressure is introduced into the cavity to pressurize the body. The process can be used for sintering and/or hot isotactic pressing of bodies made of ceramic powder and for similar purposes.

U.S. Pat. No. 5,072,087, granted Dec. 10, 1991, describes a process for preparing a heat-treated body from a material (preferably a dielectric ceramic) that does not couple well with microwaves while nevertheless using microwave energy for the heating step. The process involves the use of a microwave susceptor (i.e., a material that couples well with microwaves) as a means for generating heat in the material. To avoid contamination of the final product, a susceptor is chosen which is converted, during the heating step, to a substance which is substantially the same as the material itself, both the susceptor and the material are converted to the same desired final product, or the material is converted to a substance substantially the same as the susceptor. The resulting substantially heat-treated (and preferably sintered) bodies can be used for a variety of purposes, e.g., as substrates for micro-electronic devices. The process can also be used for joining bodies of nonsusceptor materials.

In U.S. Pat. No. 5,164,130, granted Nov. 17, 1992, a method for sintering ceramic materials is described. A ceramic article is coated with layers of protective coatings such as boron nitride, graphite foil, and niobium. The coated ceramic article is embedded in a container containing refractory metal oxide granules and placed within a microwave oven. The ceramic article is heated by microwave energy to a temperature sufficient to sinter the ceramic article to form a densified ceramic article having a density equal to or greater than 90% of theoretical density.

U.S. Pat. No. 5,202,541, granted Apr. 13, 1993, discloses a method of heating a workpiece assembly and a load assembly suitable for heating by the method. The method involves heating the workpiece assembly in a microwave cavity surrounded by one or more rings made of electrically conductive material. The rings fix the electrical field in such a way that uniform heating of the workpiece assembly can be achieved. Large workpieces or assemblies can be heated and, if sinterable, sintered in this way without the problems normally caused by lack of uniform fields when microwaves are used to heat large loads.

U.S. Pat. No. 5,223,186, granted Jun. 29, 1993, describes a method of sintering nanocrystalline material wherein the nanocrystalline material is microwaved to heat the material to a temperature less than about 70% of the melting point of the nanocrystalline material expressed in degrees K. This method produces sintered nanocrystalline material having a density greater than about 95% of theoretical and an average grain size not more than about 3 times the average grain size of the nanocrystalline material before sintering. Rutile $TiO_2$ as well as various other ceramics have been prepared. Grain growth of as little as 1.67 times has resulted with densities of about 90% of theoretical.

U.S. Pat. No. 5,321,223, granted Jun. 14, 1994, discloses a method of sintering a material with microwave radiation that comprises coating with microwave-absorbent carbon a compacted article comprising inorganic particles having poor microwave coupling characteristics at room temperature. The microwave-absorbent carbon does absorb microwaves at room temperature. Thereafter, the compacted article is irradiated with microwave radiation to heat the compacted article by microwave absorption of the microwave-absorbent carbon coated on the compacted article to a temperature sufficient for the inorganic particles in the compacted article to absorb the microwave radiation and for a period of time sufficient to sinter the compacted article and to remove the microwave-absorbent carbon coated on the compacted article.

U.S. Pat. No. 5,365,042 granted Nov. 15, 1994 describes a heat treatment installation for parts made of a composite material having a ceramic matrix and including a treatment enclosure which is connected to a microwave generator by a waveguide and which includes a press for hot pressing a part to be treated in the enclosure and a gas source for introducing a protective gas into the enclosure.

U.S. Pat. No. 5,521,360, granted May 28, 1996, discloses a variable frequency microwave heating apparatus designed to allow modulation of the frequency of the microwaves introduced into a furnace cavity for testing or other selected applications. The variable frequency heating apparatus is used in a method to monitor the resonant processing frequency within the furnace cavity depending upon the material, including the state thereof, from which the workpiece is fabricated. The variable frequency microwave heating apparatus includes a microwave signal generator and a high-power microwave amplifier or a microwave voltage-controlled oscillator. A power supply is provided for operation of the high-power microwave oscillator or microwave amplifier. A directional coupler is provided for detecting the direction and amplitude of signals incident upon and reflected from the microwave cavity. A first power meter is provided for measuring the power delivered to the microwave furnace. A second power meter detects the magnitude of reflected power. Reflected power is dissipated in the reflected power load. In the field of microwave radiation, it is well known that microwave furnaces are typically constructed with a fixed operating frequency. It has long been known that the interactions of various materials with microwaves are frequency dependent. These interactions may include sintering ceramics.

U.S. Pat. No. 5,432,325 granted Jul. 11, 1995 discloses an apparatus and method for high temperature sintering of plate-shaped articles of alumina, magnesia, silica, yttria, zirconia, and mixtures thereof using microwave radiation. An article is placed within a sintering structure located within a sintering container which is placed in a microwave cavity for heating. The rates at which heating and cooling take place is controlled.

Many ceramics, such as alumina, are poor absorbers of microwave energy at low temperatures. Clay and kaolin raw material are better microwave absorbers at low temperatures. When any green ceramic component approaches a critical temperature, it rapidly begins to absorb microwave energy. However, the surface, from which heat can be lost in ambiance in a microwave-only situation, rapidly becomes cooler than the center of the components. It may cause cracking and non-uniformity in material properties.

UK Patent No. 2,296,173 (EA Technology Ltd.) describes a process for microwave-assisted processing of ceramic products. The process uses conventional heat sources if necessary to elevate the temperature of the ceramic products at which microwave energy is effective in heating the ceramic products and also to compensate for the heat lost from the surfaces of the ceramic product from the volumetric heat supplied by the microwaves.

SUMMARY OF THE INVENTION

It is an object of the present invention to provide a process for the preparation of ceramic products, particularly large-sized, thick-walled products.

It is an object of the present invention to provide a more efficient process for the preparation of ceramic products.

It is another object of the present invention to provide a more ecologically desirable process for the production of ceramic products.

Yet another object of this invention is to provide a process that minimizes the time and the consumption of energy to produce the ceramic products and thereby maximizes the amount of products that can be produced in the process equipment per unit of time.

It is a still further object of this invention to provide a process that results in a more uniform, i.e., higher quality, ceramic product with fewer rejects than conventional processes.

It is another object of the present invention to provide a process that can produce a containment system for the transport and long-term storage of hazardous waste, particularly nuclear waste.

It is another object of the present invention to provide a process that can produce conventional ceramic products at less cost and with fewer defects than conventional processes.

It is another object of the present invention to provide a process for novel large-sized ceramic building and structural products useful for floors, walls and roofs as well as for roads and pavements.

These objects, as well as further objects which become apparent from the discussion that follows, are achieved, in accordance with the present invention, by a process comprising the steps of:

a) selecting the ceramic composition from the group consisting of silicate materials and other metal oxides, including mullite, alumina, red clay, magnesium aluminum spinel, as well as nitrides, carbides and mixtures thereof, b) optionally adding ceramic fibers, such as alumina, boron nitride or silicon carbide fibers, to the ceramic composition, c) autoclaving the ceramic composition to increase its hydrogen form contents, d) forming the ceramic composition into the desired shape, and e) subjecting the composition so shaped to microwave energy to internally heat and thereby sinter the composition, optionally with external heat applied by means of electrical resistance or gas fired heating.

BRIEF DESCRIPTION OF THE DRAWINGS

FIG. 5 is a longitudinal cross-sectional view of a microwave-assisted hybrid tunnel kiln and an example of the corresponding temperature profile of the ceramic processing.

PREFERRED EMBODIMENTS OF THE INVENTION

The invention comprises an innovative and advanced ceramic technology for inexpensive and quality-controlled manufacturing processes for the production of unusually large-size and thick-walled ceramic products.

Figure 1:
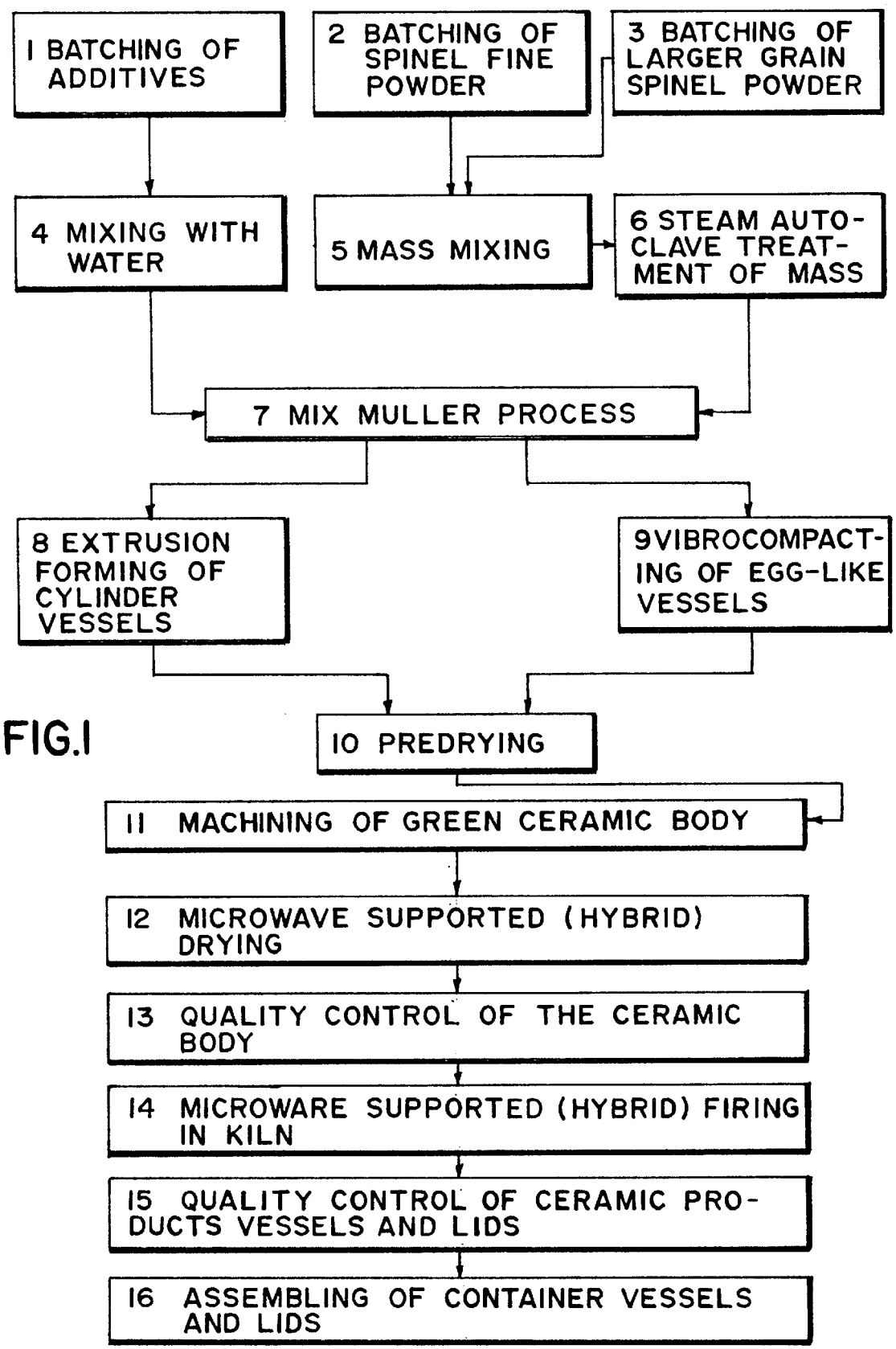
FIG. 1 is a flow chart of a preferred embodiment of the process of the invention.
Figure 3:
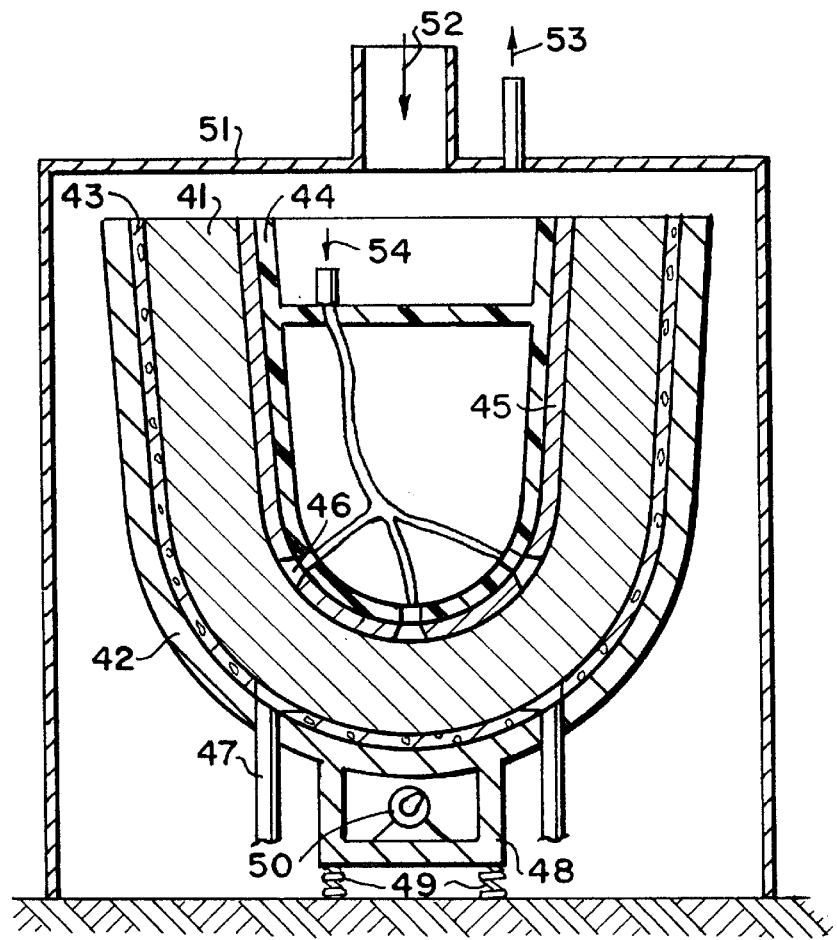
FIG. 3 is a longitudinal cross-sectional view depicting the vibrocompacting of containers of small to medium capacity.
Figure 4A:
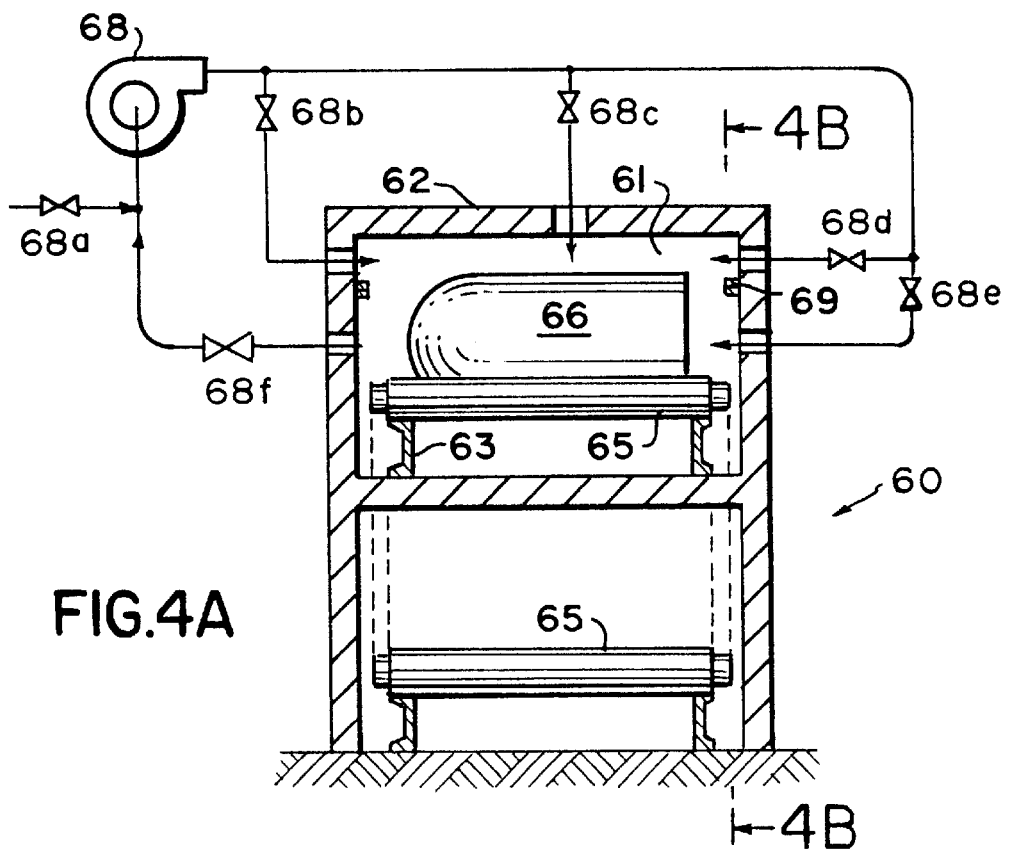
FIG. 4A is an end view of a microwave-assisted hybrid tunnel drier employing roller-induced conveyor movement of large cylindrical vessels and lids.
Figure 4B:
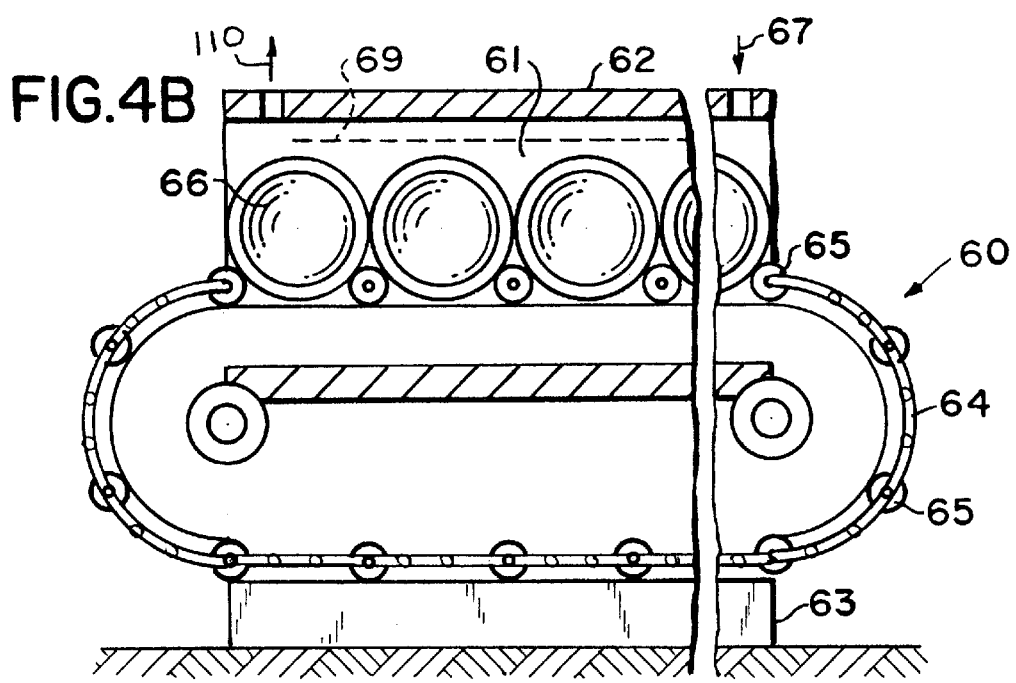
FIG. 4B shows a longitudinal cross section of the microwave-assisted hybrid tunnel drier shown in FIG. 4A.

FIG. 1 shows an over-all flow diagram of a preferred embodiment of the process of the invention, which can produce ceramic containers useful for the containerization of nuclear waste. Step 1 comprises batching of additives, plastificators, borosilicate glass, chromium trioxide and ceramic fibers and other additives. Ceramic fibers, whiskers or other fibers may be used. The additives may be present in total amounts up to about 20%. By "batching" is meant weighing out the ingredients to form a batch. Step 2 comprises the batching of fine powder ingredients for the basic ceramic composition, e.g., alumina powder, clay, kaolin, magnesium aluminum spinel. The particle sizes of the basic ceramic composition range from nanometers to a few mm. The actual optimal range of sizes is empirically determined for each ceramic component. It depends on the particular requirements of the ceramic product. Step 3 comprises batching of larger grain fractions of, e.g., magnesium aluminum spinel or alumina. The larger grain fractions may range in size to about 2 mm. Finely divided magnesium oxide lowers the sintering temperature of the ceramic composition. Another group of additives increases the plasticity of the ceramic mass, thereby making it possible to more readily form the desired ceramic product. The batch from Step 1 is then fed to a mixer where it is mixed with water in Step 4. The amount of water should be sufficient to mix, plastificate and form a homogeneous mass and yet not so much as to adversely increase the drying time. Generally, the amount of additional water or another polar liquid such as alcohol used may range up to about 18 percent of the total ceramic mass. The preferred amount of liquid ranges from about 5 to about 10 percent. In Step 5 the batches from Steps 2 and 3 are mass mixed so as to be homogeneous. The mass is subjected to a steam autoclave treatment in Step 6 for a period of time sufficient to introduce hydrogen forms into the ceramic composition in an amount that serves to increase the absorption of microwaves during heating of the ceramic up to about 800 C. In Step 7, the mass is subjected to a mix muller or attritor process. Then, depending upon the ceramic mass plasticity or whether one is preparing a container of a large capacity or a container of a small or medium capacity, the forming is conducted in alternative Step 8 or Step 9, respectively. In Step 8, containers of large capacity are preferably formed by extrusion forming of cylindrical vessels. This may be seen in FIG. 2. In Step 9 containers of small to medium size are preferably formed by vibrocompacting of, e.g., egg-shaped vessels. This may be seen in FIGS. 2 and 3. Either process of forming the containers may be used for producing the other type of container that is described above. Then the formed container from Step 8 or Step 9 is predried in Step 10 to form a green body. Preferably, the residual water in the ceramic is about 2%. In Step 11, the open ends of the container vessel and lid green body are machined to more precisely shape them. In Step 12, the machined green body is dried by means of microwave-supported (hybrid) drying, i.e., a combination of microwaves and conventional heating from either oil- or gas-fired or electric heaters, e.g., as shown in FIGS. 4A and 4B. The microwaves, which may be in the range of a frequency of about 600 GHz to about 6000 GHz are preferably at a frequency of about 700 to about 4000 GHz and at a power level calculated based on the mass of the ceramic. Preferably, the microwave energy is provided at a frequency of about 915 MHZ or 2450 MHZ. For uniformity of the microwave field, it is preferred to use two or more frequencies, e.g., 915 MHZ and 2450 MHZ. In Step 13, quality control of the ceramic body is conducted. If a defect is discovered in a unit of the ceramic product, it may be recycled in the same process line. After that, in Step 14, the ceramic body is fired in a microwave-supported (hybrid) kiln, similar to the drying means described above in accordance with a thermal schedule, e.g., as shown in FIG. 5. In Step 15, quality control of the ceramic products, e.g., container vessels and lids therefor, is conducted. The vessels and their lids are then assembled in Step 16.

To assure process and quality control of microwave ceramic processing, hydrogen forms are preferred as an effective, natural and super-clean susceptor at the beginning heating stage of microwave ceramic processing. An auxiliary technology (Step 6) provides hydrogen insertion in ceramic particles, which are used during sintering.

Ceramic mass formulation includes:
(a) determination of the chemical and mineralogical or artificial compound composition of the mass,
(b) grain-fraction composition of the mineralogical or compound ingredients, and
(c) mass preparation technique.

Preferably, the ceramic mass comprises one, two or more major components, such as preliminarily sintered and milled mullite or alumina or aluminum magnesium spinel or unmilled kaolin or clay or mixtures thereof in a range of about 80–100%. The foregoing is a basic chemical and mineralogical composition. Other additives can be added in complementary amounts of from about 2 to about 20%, which with the basic composition total 100%.

A preferred but costly addition is from about 6–12% SiC whiskers to produce a high fracture strength resistance composite—see Table 1. Additionally, SiC is also a known susceptor (absorber) of microwave, which makes it possible to induce and accelerate microwave heating of ceramics during drying and firing stages of the production process.

TABLE 1

Thermomechanical Properties of Monolithic Mullite and 20 vol % SiC-Whisker/Mullite Composition

|  | Mullite | Composite |
| --- | --- | --- |
| Young's modulus (Gpa) | 225 | 284 |
| Poisson's ratio | 0.25 | 0.24 |
| Fracture strength (MPa) | 290 | 550 |
| Fracture toughness (MPa × $m^{0.5}$) | 1.8 | 4.3 |
| Coefficient of thermal expansion ($10^{-6}/°C$.) | 5.2 | 4.80 |
| Thermal conductivity (W/m × K) | 4.9 | 7.8 |

Source: Ceramic Transactions, Vol. 19, Advanced Composite Materials. Edited by M. D. Sacks, The American Ceramic Society, 677–693 (1991).

Another preferred additive is about 2–4% of a material which should decrease the sintering temperature of the material to 1300–1350° C., producing at these temperatures a liquid eutectic. An example of such an additive is borosilicate glass powder with a significant content of alkaline metal oxides. Additionally, boron increases nuclear retention and nuclear resistance properties of the ceramics.

It is possible to add to the ceramic mass any oxide which can increase the physical or sintering properties of ceramic bodies. For enormously high levels of waste radiation, it is preferred to add to the ceramic mass composition BeO ceramic powder.

A very important role in ceramic technology is played by water, which should plastificate and bind the ceramic mass particles. As determined by a special calculation, preferred forming and drying properties of the proposed ceramic mass are obtained by about 9–14% of water content or mass moisture.

It has been discovered and employed in this invention that seven other hydrogen forms may be present in the alumina-silicate lattice and micropores and canals of the particles as well as on their surface, which significantly induces and accelerates microwave ceramic processing. These hydrogen forms may affiliate with ceramics up to about 800° C. The hydrogen forms make it possible to induce microwave absorption and the consequent heating and sintering processes of a ceramic body and to provide control and acceleration of the microwave-ceramic interaction from about 40° C.–80° C. to about 600° C.–800° C.

To furnish the effect which is mentioned above, it is preferred to insert hydrogen ionic and molecular hydrogen forms in the ceramic lattice, micro-pores and capillaries and/or by absorption by the micro-powder surface of the ceramic green mass, employing an autoclave treatment of the ceramic mass at steam pressures up to about 2.45 GPa.

A similar effect may be furnished by carbon powder additive or carbon content materials, such as SiC, as a part of the ceramic green mass. This doping works as a susceptor of the microwave-ceramic interaction.

For nuclear waste storage containers, it is necessary to maximize density and solidity (integrity) of a ceramic material after firing and to eliminate porosity. In order to prevent gas and radiation penetration through ceramic container walls, a special grain fraction composition has been developed. To accomplish this, two fractions of ceramic raw materials are preferably used. The relatively coarse grain particles comprise about 63–67% of the fraction composition. The fine grain fraction should comprise about 23–25% of the fraction composition. The remaining portion of the fraction composition comprises nanophase or kaolin particles having a size which is less than about 60 nm. This grain composition makes it possible to achieve up to about 95–99% of the theoretical density of the ceramic material.

Blending and other milling and mixing equipment provide mixing and homogenization of the raw composition that includes three to four types or more of powder and grain-size ceramic oxide raw materials, ceramic fibers (whiskers), and hot water.

The mixing method, which is described above, achieves necessary homogenization of the grain-powder mixture and less than 15% by weight of the mass as moisture, which is important to decrease heat consumption and time period of the drying process.

To increase ceramic mass homogenization and to provide air evacuation from ceramic mass which results in an increased product quality, additional mass blending (mixing) may be coupled with a vacuum treatment.

To increase the quality of the containers of the invention, both ceramic vessel and lids are prepared at the same time and both of them are marked as two parts of a single container.

Figure 2:
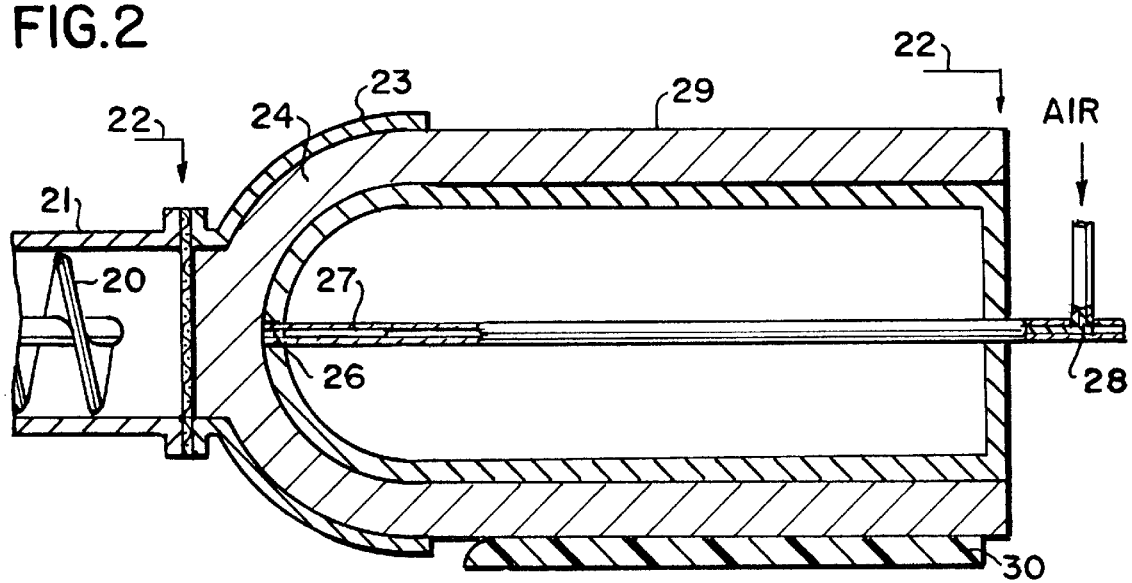
FIG. 2 is a longitudinal cross-sectional view depicting the extrusion of cylindrical containers of large capacity.

FIG. 2 is a cross-sectional longitudinal view depicting the extrusion of a container 29. Through the extruder outlet 21, the auger 20 extrudes the ceramic mass 24 between cupping die 23 and kernel 25, which is held in place by pusher stock 28. The cupping-die 23 and the kernel 25 make it possible to produce cylinder-shaped vessels of containers with spherical bottoms or spherical lid-covers. The resilient curved underpan 30 receives the cylindrical container 29. After the cylindrical container 29 has been formed to the desired length, the wire saw 22 is used to sever the cylindrical container 29 at the extruder outlet 21. A wire saw 22 is also used to trim the end of the cylindrical container 29 at its open end. Then air is introduced into air tube 27 and released through air valve 26 in order to release the kernel 25 from the inside of the ceramic body 29. The kernel 25 is removed from the ceramic body 29. Finally, the underpan 30 is used to provide safe transportation of the green-formed cylindrical container 29 to the next process stage, the dryer—as shown in FIGS. 4A and 4B.

To decrease moisture content and increase pristine strength and homogeneity of the large cylinder-like containers, their body parts are predried at a temperature less than about 90° C., employing microwave assisted internal heating and volumetric convective external (surface) heating.

Vibrocompaction is another method that may be used to produce a body shape for the container. In that method, a ceramic mass is loaded and compacted in a special form, using a vibrator in order to maximize density of the ceramic body. FIG. 3 is a vertical cross-sectional view depicting the vibromolding of a container of small to medium capacity. Ceramic mass 41 is placed in the space between water-permeable porous shell 43, which is contained in outside metal frame formed of at least four ribs 42, and water-impermeable inner shell 45, in which rests inner plastic rib frame 44. Vibrator frame box 48 is attached to outside metal frame 42, rests on vibration absorber 49, and houses vibrator 50. When activated, vibrator 50 compacts the ceramic mass 41. After compaction of the ceramic mass 41, air valves 46 are opened and compressed air is introduced through openings in the inner plastic rib frame 44 and the water impermeable material 45 in order to release the inner plastic rib frame 44 and the water impermeable inner shell 45 from the formed ceramic mass 41, from which they are then removed. The whole vibromolding apparatus is contained within removable metal jacket (casing) 51, in the top of which is located a microwave waveguide inlet 52. Microwave waveguide inlet 52 serves to introduce microwave energy into the removable metal jacket (casing) 51. The microwave energy is used to predry and dry the ceramic mass 41 in the form of an egg-shaped container. The water released from the ceramic mass 41 during the predrying or drying step is removed from the removable metal jacket (casing) 51 by means of vacuum outlet 53. After the predrying or drying step, the removable metal jacket (casing) 51 is removed from the vibromolding apparatus. Pusher 47 is used to release the predried ceramic mass 41 in the form of an egg-shaped container.

To avoid additional movement and obtain effective processing of the egg-like container products, forming, predrying and drying processes are combined in one apparatus as shown in FIG. 3. When vibrocompacting forming of the container is finished, the same form serves during a predrying process which is provided using microwave energy. The metal casing 51 protects personnel from microwaves.

An outside wall of the container body is produced from porous water-permeable porous shell 43, which makes it possible to dry the ceramic. To form the particular shape of the ceramic item, an inner surface of the form is produced from water-impermeable inner shell 45—see FIG. 3.

An outside wall of the container form is produced with a few small holes. These holes make possible an air input between ceramic body and form wall to liberate ceramic body and remove this ceramic semi-product after drying process.

To uniformly increase the density and strength of the ceramic body during drying process of the small and medium container bodies, a vacuum pump is employed, the outlet for which is shown as 53 in the FIG. 3.

The microwave-assisted or hybrid drying process makes it possible to increase the efficiency of the drying process and the quality of the thick-walled product, providing precise control of the intensity of ceramic heating. Preferably, heating of the ceramic body at about 20° C.–100° C. is provided by microwave energy.

In order to furnish an appropriate heating rate of the dryer walls and ceramic item surface and to remove water from the ceramic item surface with an external heat compensation of the water vaporization from the ceramic body, both hot gas/air mixture from a convection system and conventional electrical heater sources are employed together with microwave heat sources.

Another and very effective construction of the dryer uses a roller conveyer for the horizontal movement of ceramic vessels and lids during thermal processing. This equipment achieves a high rate of productivity for industrial manufacturing—see FIGS. 4A and 4B.

FIG. 4A is an end view of a microwave-assisted hybrid tunnel drier 60. Drying chamber 61 has a wall 62. On the frame 63 of the dryer 60 is mounted the Bush roller chain 64 (seen in FIG. 4B). Rotating rollers 65 bean, rotate and move ceramic cylinders 66. Elements of the electrical heaters 69 are used to supplement the heating provided by the microwave radiation. Blower fan 68 is used to provide a hydraulic thermal exchange circulation system, controlled by valves 68a–68f. Air is supplied to blower 68 by means of valve 68a. Blower 68 then delivers the air to drying chamber 61 via valves 68b to 68e. The heated air from the dryer is recycled to the blower 68 via valve 68f.

FIG. 4B shows a longitudinal cross section of the microwave-assisted hybrid tunnel drier 60 shown in FIG. 4A employing roller-induced conveyor movement of large cylindrical vessels and lids 66. Drying chamber 61 has a wall 62. Bush roller chain 64 provides conveyor movement to rotating rollers 65 that bear, rotate and move ceramic cylinders 66. Microwave waveguide inlet 67 serves to introduce microwave energy through the wall 62 of the dryer 60. The microwave energy is used to dry the ceramic cylinders 66. The water released from the ceramic cylinders 66 during the drying step is removed from the drying chamber 61 by means of an outlet 110 in the wall 62 of the dryer that is remote from the microwave waveguide 67.

Movement of a cylindrical ceramic item is provided in horizontal position by rotated rollers 65, using metal continuous chain 64. These rollers 65 are horizontally positioned and rotated in perpendicular direction of the ceramic vessel 66—FIG. 4B. The rollers 65 have a diameter size and a gap between two rollers 65 that are less than the diameter of the ceramic vessel 66.

The application of microwave energy sources in combination with electrical resistance heaters and/or gas burners and hot air-gas mixture which is supplied by the special hydraulic system permits thermally effective and uniform treatment of ceramic items in correspondence with an appropriate thermal-time schedule of the ceramic production. Microwave-assisted or hybrid firing increases the efficiency of the firing process and the quality of the product. Internal heating and sintering of the ceramic item body from 40° C. to 1350° C. is provided by microwave energy. Meantime, an appropriate heating of the thermal aggregate walls and the ceramic item surface is provided by the hot gas/air mixture that is delivered to the dryer and electrical resistance heaters and/or gas burners sources.

FIG. 5 is a longitudinal cross-sectional view of a microwave-assisted hybrid tunnel kiln 70 and an example of the corresponding temperature profile of the ceramic processing. Tunnel kiln 70 has a multilayer wall 71 that includes refractory materials and a metal casing to prevent the escape of microwave radiation. The kiln cars 73 enter the tunnel kiln 70 from the left and ride on rail road 72. Microwave waveguides 74 serve to introduce microwave energy through the wall 71 of the kiln 70. The microwave energy is used to fire the ceramic containers assisted by electrical resistance heaters 82.

Blower fan 75 uses a manifold for the hydraulic thermal exchange circulation system. Blower fan 76 uses a manifold for the hydraulic air-cooling circulation system. The hydraulic system is provided by blower fans 75 and 76 and chimney 77. Fan 76 blows outside air into the cooling zone 70c through multiple injection nozzles in the ceiling of the zone to surround the vessels 91. Some of the injection nozzles are aimed vertically downward and some of the nozzles are directed to provide air flow countercurrent to the travel direction of the vessels 91. Fan 75 takes hot air from the beginning of the cooling zone and delivers it to the heating zone 70a and the firing zone 70b. Outside air is taken in by fan 75 and used to control the temperature of the heating and firing zones, 70a and 70b respectively. Part of the heated air may be delivered to the dryer, which may be a separate unit. This method decreases energy consumption and increases the thermal efficiency of the system. In addition, the system serves to maintain the tunnel kiln at a pressure slightly below the atmospheric pressure for safety purposes and to decrease loss of heat. Chimney 77 exhausts the gaseous output of the kiln 70 assisted by chimney injector 78, which is fed by the manifold of the blower fan 75. The top of chimney 77 is covered by deflector 79 in order to prevent rain impact. Metal net curtains 80 are used to separate the cooling zone from the heating and firing zones, 70 and 70b, of the tunnel kiln 70. The ceramic containers enter the kiln 70 through metal door 81. Shown above the depiction of the kiln 70 is a profile of the temperatures at the different points within the kiln, ranging from 60 C at the entry point, rising to 600 C, then 1360 C, and falling to 300 C at the exit of the kiln.

Figure 6:
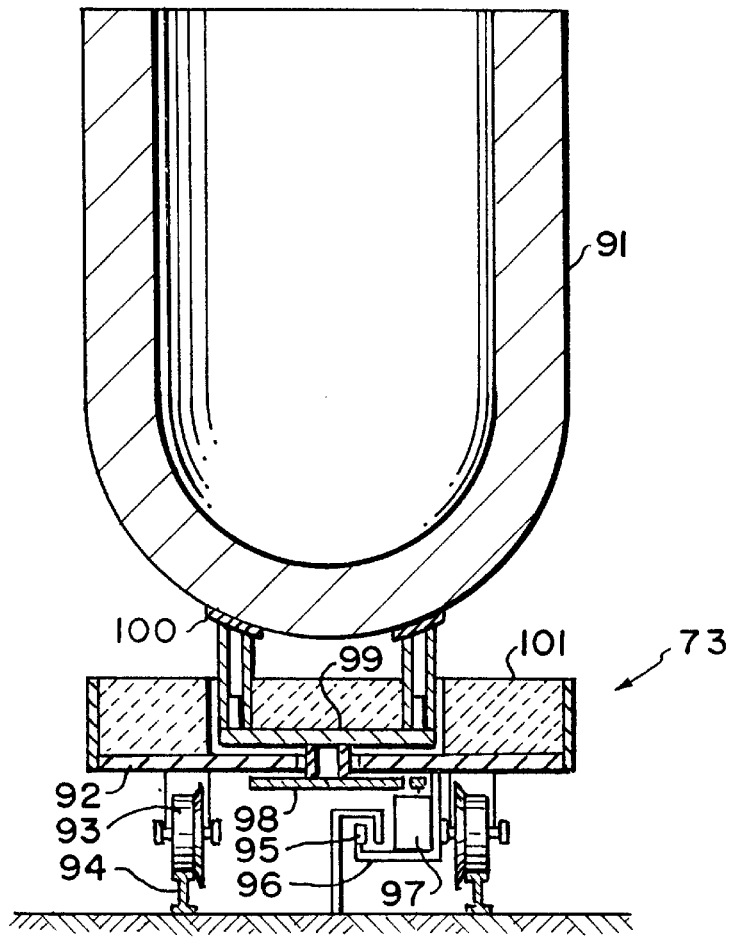
FIG. 6 is a vertical cross-sectional view of a tunnel car used in the tunnel kiln shown in FIG. 5. On the tunnel car is a ceramic container vessel or its lid, shown in cross section.

The kiln car 73 is shown in cross section in FIG. 6. In FIG. 6, 6, a shuttle movement of the ceramic vessel 91 is provided by the kiln car 73. This car 73 has a ring-like refractory platform 99, which is capable of vertically rotating the ceramic vessel 91. Kiln car 73 transports ceramic vessel 91 through the tunnel kiln 70, where firing of the ceramic container vessel and its lid takes place. The tunnel car 73 has a metal base frame 92 on top of which is placed thermal refractory insulation 101 and to the underside of which are mounted metal wheels 93, which ride on rails 94. A ceramic container vessel 91 (or lid) rests on ground parts 100 of the refractory setting frame, which are joined to rotating dish-platform 99. A shaft passes through an opening in the metal base frame 92 of the tunnel car and extends between the rotating dish-platform 99 and revolving mechanism 98 to which it is joined. The revolving mechanism 98 is driven by electrical motor 97, which gets its power from an electrical current bar-rail source 95 by means of electrical contact brush 96.

Rotation of the ceramic product around its axis in vertical position on the car-platform results in a uniform impact of the thermal sources. The kiln car has a ring-like refractory dish-platform and refractory frame setting which stabilize the ceramic item during car movement. To provide uniform thermal treatment, a ring-like platform and setting frame of the car which bears the ceramic item is rotated by an individual electrical motor. Electrical current is taken by electrical contact brush from a current bar-rail which is positioned parallel to the rail road.

Microwave energy is delivered by a few microwave guideways. They come through, for example, the ceiling of the tunnel in the area of the temperatures between 300° C. and a maximum temperature of the thermal processing.

A uniform impact and a deep penetration into a ceramic body is achieved by a few other microwave sources at two or more different frequencies of the waves.

To increase microwave impact and to save refractory costs, the beginning part of the tunnel preferably has an inner metal screen-shell. This shell is preferably cooled by running water.

A technique has been developed which prevents microwave—ceramic item interaction and heating of the ceramic item in the cooling zone of the kiln and makes possible air flow from the cooling zone to the sintering and heating zones. The technique comprises the use of one or a few removable and elastic metal nets 80 positioned within the tunnel 70. These metal net curtains 80 have small cell sizes and these cell sizes are less than half of the microwave wavelengths. These elastic metal net curtains 80 touch and slip off the ceramic items 91 on the cars as they travel through the tunnel.

To prevent microwave poisoning impact, all thermal aggregate is covered by a metal shell-jacket. For the same purpose, one or both ends of the thermal aggregate are equipped with additional chamber rooms at both ends of the thermal aggregate, and each chamber has automatically closed doors whereby an open position of the outside door strictly corresponds to a closed position of the inside door.

Additionally, it is possible to provide final cooling of the ceramic items from a surface temperature 200° C.–300° C. to room temperature, using natural conditions and ordinary fans on the shop floor.

Both vessel and lid junction parts are machined for the first time after predrying in order to provide a necessary geometrical shape and a roughened surface of both clutched parts. Both vessel and lid joining surfaces are additionally machined to obtain a dense set of the micro and macro furrows and grooves which makes it possible to absorb the powder of the ceramic joining compound.

Vessel and lid have one or more ring ridges and grooves on both joined ends of the container vessel and lid and these ridges and grooves completely coincide to produce a unified container. Each ridge and groove has in cross-sectional view either a triangular or trapezoidal form. The height of the triangular or trapezoidal ridges and the depth of the corresponding grooves may be up to one thickness of the ceramic wall of the container.

These ridges and grooves on the ends of the vessel and lid walls are produced as a part of the ceramic container production process using three steps:

1. the shaping of the ends of both vessel and lid as a part of the ceramic green mass forming process so that the ends mate,
2. the joining surface areas are checked and machined after the drying process
3. the joining surface areas are checked and machined after the firing process to obtain full coincidence assembling of the vessel and lid parts of the container.

Figure 7:
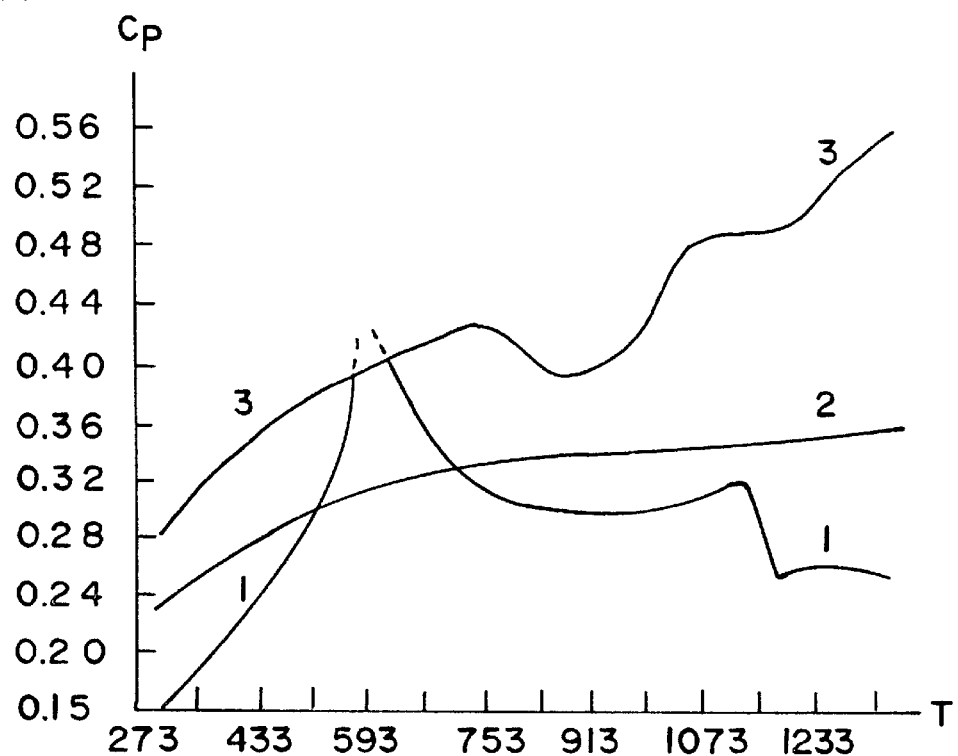
FIG. 7 is a graph of experimental curves obtained by quantitative thermography of the dependence of the heat capacity of samples of perlite on temperature.

FIG. 7 is a graph of experimental curves obtained by quantitative thermography of the dependence of the heat capacity of samples on temperature (the error in the determination of $c_p$ in the temperature range 300–1350 K is not higher than ±3%). $c_p$=heat capacity (cal/g deg), and T=temperature (K). Curve 1 represents a sample of the original perlite rock from Mukhor-Tallin location. Curve 2 represents the same sample after preliminary ignition at 1323 K. Curve 3 represents a sample of perlite, similar to the first sample, but thermally processed (swollen) under the following conditions of the first and second stages: 1) 603 K and holding time of 12 min, with removal of 2.65% of water; 2) 1323 K and 40 sec holding time.

Figure 8:
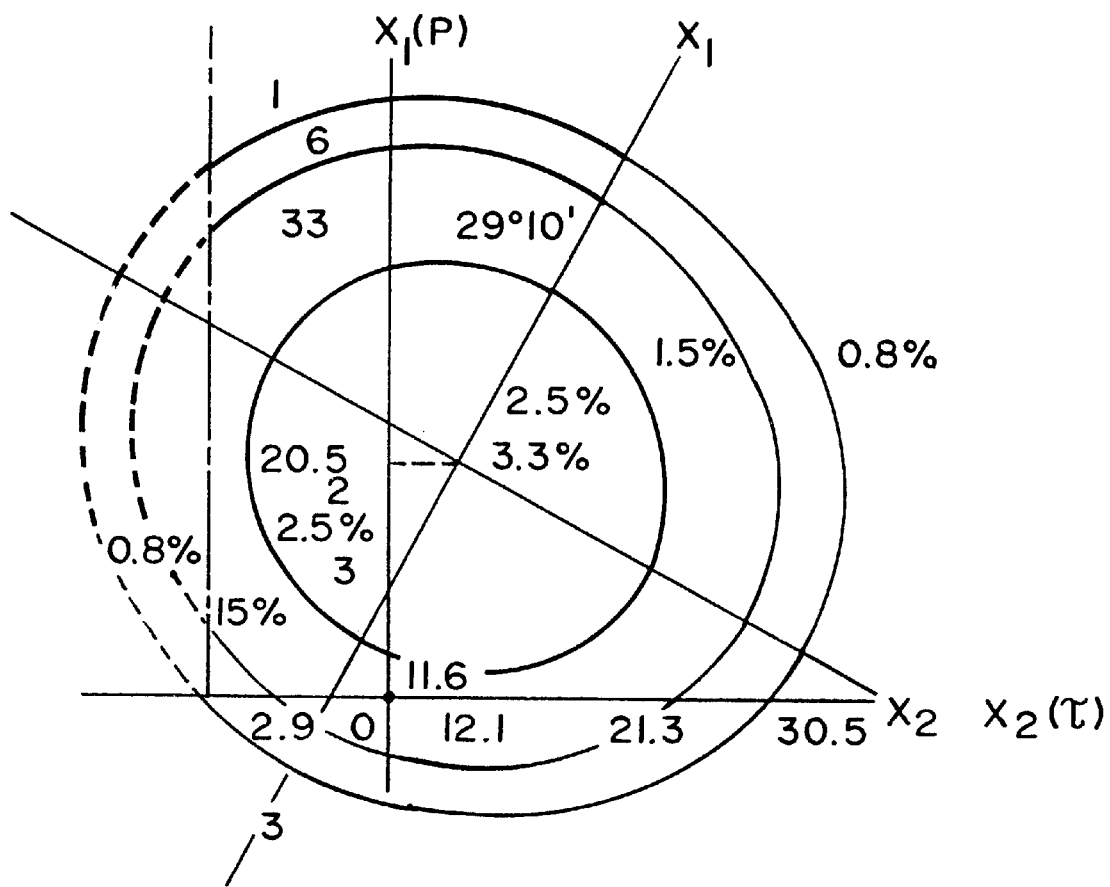
FIG. 8 shows isolines of relative perlite granules additional weight, including granules which have been treated in an autoclave (except for hygroscopic liquid).

FIG. 8 shows isolines of relative additional weight of perlite granules, including granules, which has been treated in an autoclave (except for hygroscopic liquid):

1—isolines of response values;
2—border of real function existence;
3—illustrative curves of estimated response values beyond real function existence.

Material increase in weight is determined according to formula:

$$Y = \frac{g_2 - g_1}{g_1}\% = 1.947 + 0.916x_1 + 0.357x_2 - 0.172x_2 - 0.151x_1^2 - 0.034x_1x_2,$$

where $x_1$, $x_2$=factors of levels

It is possible to control and vary both the composition and properties of a ceramic product in order to obtain all necessary refractory, chemical and nuclear resistance/retention properties in combination with the mechanical properties of the shaped item.

The hardening or sintering ceramic process is accompanied by volume variations which depend on the properties of the particular raw materials. These volume variations appear at appropriate temperatures and stimulate ceramic body stresses and volume shrinkage which create serious problems for ceramic processing, especially for articles having a large or precision shape.

Because microwave energy is absorbed simultaneously throughout the work-piece (microwave heating acts internally within the bulk), microwave energy can provide uniform heating of the entire ceramic unit. As a consequence, microwave energy eliminates thermal gradients which produce stresses and cracking during heating, as may occur in conventional processing by external heating.

One proposed advantage of the microwave heating phenomena is the ability of microwaves to provide instantaneous penetration in the ceramic body which results in uniform ceramic body shrinkage during the densification and sintering processes. Uniform shrinkage of the ceramic mass permits the inexpensive production of large ceramic units. Microwave assisted (hybrid) internal ceramic heating presents a unique opportunity for ceramic technology to bring to the market new large (and specially shaped) products with special properties and at reasonable cost.

An advantage of microwave ceramic processing is the possibility of internally joining and sealing ceramic materials because of the transparency of the materials to microwave energy. Moreover, using appropriately processed powder, high temperature microwave heating can provide coating, covering, enameling, and glazing of ceramic and metal materials.

A microwave tunnel furnace (kiln) may be fully controlled to provide a versatile and sensitive adaptation of the firing and cooling modes. All industrial processing can be done on a conveyer, which makes it possible to automate the technological operations of the forming, drying and firing stages.

Current accomplishments in microwave ceramic processing are described, for example, in Ceramic Transactions, Volume 59, "Microwaves: Theory and Application in Materials Processing III", Edited by D. E. Clark, D. Folz, S. J. Oda and R. Silberglitt. The American Ceramic Society, Westerville, Ohio, 1995.

This invention employs a discovery that hydrogen forms and/or carbon that are present or are inserted in a ceramic micro and macro structure play an important role to induce, stimulate, and control microwave ceramic processing, depending on the chemical properties and physical conditions of oxide, carbide and nitride ceramics. The phenomena which have been discovered would also permit in-site joining of the ceramic parts (cup-vessel with a lid-cover) of multi-purpose container.

The invention includes an advanced microwave furnace which comprises an industrial kiln to provide ceramic heating, sintering and joining of the container parts at 1200° C.–1600° C. Microwave thermal processing has the potential to be 15–30 times faster than conventional firing processes because ceramics can absorb more than 95% of the microwave energy delivered.

In the right formulations, almost any ceramic material may be used in the process of the invention. However, for production of multi-purpose ceramic container vessels and lids, four types of ceramic materials are preferred as the most suitable materials. They are mullite ($3\ Al_2O_3 \times 2SiO_2$), alumina ($Al_2O_3$), magnesium aluminum spinel ($MgAl_2O_4$), and red clay. The ceramic mass may also contain grain and powder additives, such as zirconia or borosilicate glass, and ceramic fibers, such as SiC and BN. The radionucleide accommodation, retention and radiation insulation properties of these materials increase from mullite to Synroc ($CaZrTi_2O_7$). However, the production and raw materials costs of these products are increased by the same order with a tremendously increased factor for Synroc.

The choice of raw ceramic materials should take into account the following:
  (i) customized properties desired for particular products,
  (ii) costs of natural or artificial resources, and
  (iii) technological aspects, including forming and thermal treatment stages.

Conventional or ordinary red clay is the raw material of choice for the structural clay products industry. Ordinary clay is one of the more useful and inexpensive natural materials. The composition and properties of red clay vary with the nature of the deposit. A mixture of various silicate materials is mostly used for clay brick, roof tile, drainage and sewerage pipes and pottery products. Many types of clay have an excellent plasticity which permits easier forming processes.

Kaolin is a type of clay which has an especially stable and homogeneous chemical and mineralogical composition. Kaolin mineral homogeneity is important for microwave firing because the uniformity of microwave heating depends on homogeneity of the ceramic starting materials. Kaolin based products include whiteware, china, electrical ceramics, refractories and composite engineering construction ceramics. An example of an advanced composite is a mullite matrix with boron nitride fibers.

Kaolin is a relatively inexpensive natural material with lattice hydrogen content. It has a plasticity property and can absorb hydrogen forms through the surface and, accordingly, permits the use of extrusion and casting for forming processes. The major part of the chemical composition of the raw material, kaolinite, is $Al_2O_3 \times 2SiO_2 \times H_2O$, which is called kaolin.

Kaolin is used in numerous ceramic applications where its refractive, Theological properties and fired whiteness are important. Kaolin is widely used for china, tile, chemical equipment, electrical insulators, and sanitary wares. The production of refractories from kaolin is a well-known technology. For example, one U.S. kaolin deposit consists of 55.2% $SiO_2$, 27.9% $Al_2O_3$, 12.6% of the weight (mainly "water") is lost on ignition, and the remainder consists of the following oxides: $TiO_2$, CaO, MgO, $K_2O$, and $Na_2O$. Sintering by conventional external heating occurs at about 1350° C. by the major reaction:

$$3(Al_2O_3 \times 2SiO_2 \times 2H_2O) \rightarrow 3Al_2O_3 \times 2SiO_2 + 4SiO_2 + 6H_2O,$$

where $Al_2O_3 \times 2SiO_2$ has the form of mullite crystals which are homogeneously mixed with silica glass.

Some types of kaolin have exceedingly small grain powder sizes. This powder may absorb large quantities of water which results in a swelling of the material and makes for a difficult forming process. Therefore, a mixture of kaolin with conventional clay and ignited kaolin is preferred as one starting material in the process of the invention. Ignited kaolin or preliminarily preformed mullite are inert to water and may substantially increase the forming property of the mixture. Additionally, ignited inert ceramic granules decrease body volume variations during low and high temperature thermal processing.

Kaolin raw material can be a base to artificially produce (sinter) a mullite mineral. Kaolin is a well-known and widely used chemically and mineralogically homogeneous raw material with a reasonable low cost of mining and preliminary treatment. Mullite-content material embodies refractory and armor properties and it is used as a material that is resistant to mechanical, electrical, thermal and chemical stresses in extreme and aggressive technological situations, including some combination of them within a chemical reactor or a metallurgical vessel. Because it contains a substantial percentage of alumina oxide, mullite can retain and insulate radionucleides without a serious change of the chemical and mechanical properties of the initial material and unit shape during millions of years in any adverse conditions, including combined thermal-radiation impact.

It is possible to increase the nuclear insulation properties of ceramic materials. For example, by adding $Al_2O_3$, MgO, $ZrO_2$ or BN granules or fibers to the ceramic mass, the nuclear-retention property of the mixture is increased several times, and therefore makes it possible to decrease the thickness of the container walls.

Adding other ceramic fibers to the ceramic body substantially increases the mechanical properties of a multi-purpose container material. For example, the insertion of BN continuous fibers provides a superior composite material because BN is the best artificial material for nuclear retention and insulation, tensile strength, fire and electrical resistance and other chemical and mechanical properties. The aforementioned materials and compositions are selected and ranged in consideration of their costs and manufacturability when there are a lot of other ceramic materials. Table 2 compares the physical and mechanical properties of other ceramic and metal materials, and demonstrates that ceramic materials can have perfect mechanical and other properties which makes them suitable for a multi-purpose container.

Table 2 also shows the greater compressive and tensile strength, fracture and crack resistance of ceramic materials in comparison with steel, especially by reason of the fact that at 300° C. the tensile strength of metals usually decreases by 1.7–2.0 times whereas mullite refractors and other ceramics have the same tensile strength as at room temperature.

Alumina and kaolin materials and their fiber reinforced compositions may be selected and ranged in consideration of their costs and manufacturability when there are a lot of other ceramic materials. Table 2 compares the physical and mechanical properties of three ceramic materials and demonstrates that ceramic materials can have perfect mechanical and thermal properties, which make them suitable for a multi-purpose container.

TABLE 2

Characteristics of Three Typical Engineering Ceramics

| Items | SiC | AL$_2$O$_3$ | MgO$_x$Al$_2$O$_3$ |
|---|---|---|---|
| Density (g/cc) | 3.1–3.2 | 3.90–3.99 | 3.59 |
| Bend strength (MPa) | 400–700 | 300–450 | 120–150 |
| Thermal conductivity (W/m × K) | 50–170 | 20 | 14 |
| Thermal expansion coeff. (10$^{-6}$/K) | 4.3–4.8 | 8–9 | 6.7 |
| Hardness (Hv) | 2400 | 1500 | |
| Elastic modulus (GPa) | 400–480 | 320–370 | 220–250 |
| Fracture toughness (Mpa × m$^{1/2}$) | 3–5 | 2–3 | Poison's Ratio: 0.29 |
| Material costs (estimation in $/kg) | 25–40 | 0.7–1.0 | 1.0–1.3 |

Source: Ceramic Materials and Components for Engines. Edited by V. J. Tennery, Amer. Cer. Soc., 1480–94 (1989).

Although the process of the invention may be used to produce any ceramic products, particularly large-sized, thick-walled ceramic products, it is especially well suited to the production of multi-purpose containers. Therefore, the production of such products is emphasized herein. However, the specific description with respect to the production of multi-purpose containers is also generally applicable to the production of any other ceramic product.

The multi-purpose container are preferably produced with two shapes of the container vessel, which depends on the shape, size and conditions of the loaded solid waste products:

A. a cylindrical vessel of large capacity, for example, for fuel rods of an atomic power station and B. an egg-like (ellipsoidal or spherical) vessel of small or medium capacities for any bulk, lump or grain waste materials and contaminated devices.

The inside and outside shapes of the container vessels and lids may be any combination of the spherical, ellipsoid and cylinder forms. An ellipsoid or spherical shape is preferred for the ends of the module size containers with a capacity in the range of 0.5 m$^3$ to 10 m$^3$. Small and medium capacity containers are similar to eggs; whereas the large capacity containers have more or less length in a cylindrical part. This form permits uniform body variations caused by production processing of ceramic vessels and lids, their thermal joining and during thermal expansion due to radioactive heating. Also some small swelling may occur under long term radiation impact.

To provide universal services, the containers can be produced with different inner capacities, for example, small capacities from about 0.1 m$^3$ to about 0.75 m$^3$, medium capacities in the range of about 1 m$^3$ to about 2.5 m$^3$, and large capacities up to about 10 m$^3$ and more. The diameter size of the multi-purpose container which can be varied from about 250 mm to about 1200 mm permits the loading of large-size blocks or contaminated parts of other equipment into the multi-purpose container.

The capacity of the multi-purpose container optimizes interim loading time when the multi-purpose container is used for other nuclear waste sources, directly at the site. Additionally, the shape and size of the multi-purpose container-package is determined by transportation and repository requirements. The wall thickness of the multi-purpose container should be in the range of about 60 mm to about 150 mm because these walls are a barrier for radio-nucleides and must withstand all possible mechanical impacts which may occur during transportation or in the repository.

There are other anticipated environmental benefits. For example, microwave ceramic processing is an especially environmentally clean technique and does not cause the air or water pollution that is produced by traditional ceramic and metallurgical plants. There are no fossil-firing exhausts and no water or air pollution such as fluorine gas emissions due to the rapid and uniform thermal processing of clay products. Broken and destroyed ceramic products can be returned to the same ceramic plant to be used as a part of the raw materials mixture.

Table 3 below shows the benefit in energy expenditure from microwave ceramic processing. According to experimental data from this preliminary study, microwave ceramic processing can decrease the sintering-processing temperature by 100° C.–200° C. and reduce the processing period by 20 times.

The capital cost to design, construct, produce and install a microwave conveyer kiln, machinery and equipment for ceramic mass preparation, forming, drying, firing, and product transportation is less than that of traditional kilns for structural clay products, electrical porcelain insulators or whitewares because of the elimination of thick refractory insulation shells and reduction of kiln length.

TABLE 3

Comparison of new and conventional techniques for ceramic firing process

| Product and process at 1050° C. | Theoretical energy consumption KwH/lb | Duration of treatment Hours | Efficiency coefficient | Cost of energy per cubic foot $ |
|---|---|---|---|---|
| Brick production by fuel firing | 0.120 | 20.0 | 0.3 | 6.93** |
| Microwave-ceramic processing (experimental data) | 0.120* | 1.0 | 0.6 | 5.08*** |

\* = Real energy consumption is less because part of the raw materials is chemically inert to reduce ceramic body volume variation;
\** = Actual data from "American Ceramic Society Bulletin", No. 1, 1993, p. 20;
\*** = The calculation of the price of electricity at $0.12 per one KwH.

The major part of ceramic technology which defines ceramics as an independent part of science and technique is the unconvertible densification as a result of thermal treatment. This treatment is often separated into two stages: drying and firing. Drying results in preliminary ceramic densification due mainly to adhesion of ceramic particles when the liquid binding (water, e.g., polar organic liquid) is removed. The main goal of ceramic drying is the preparation of shaped ceramics for loading and handling inside a ceramic kiln (furnace). Many technologies combine low and high temperature ceramic treatment in one aggregate. Low temperature drying can utilize the surplus heat of high temperature ceramic firing.

The ceramic firing process is unique to the creation of ceramic materials and products. Firing produces ceramic sintering and stone-like densification. Sintering may involve a number of processes simultaneously, including diffusion, chemical interactions, melting and volumetric change, depending on the particular mineral composition employed. These characteristics are known in general and also for each isolated phenomenon. However, the sintering of ceramics is a multi-faceted process due to interactions between three phases: solid, liquid, and gas. These interactions involve chemical reactions, diffusion, mechanical movements of the particles, evaporation, and absorption. All of these actions are induced by a thermal stream. The speed and power of the heating, i.e., the thermal stream, determine the dynamics and kinetics of the sintering process. Therefore, ceramic thermal absorption can often describe the kinetics of ceramic densification and sintering processes.

Other types of thermally activated processes must be accomplished, accommodated or avoided to provide ceramic processing. During a particular ceramic densification and sintering, the same thermal cycle that causes positive densification and particle bonding also may lead to unexpected shrinkage and other negative processes. Binder burnout, volatile gases removed, phase transformations, pore and grain growth and/or reduction occur during ceramic firing. Another very important factor is the micro-and macro-heterogeneity of the initial ceramic mass. Even "pure" kaolin has many accompanying impurities. Artificial one-component raw materials that are used for advanced (engineering) ceramics also have inhomogeneities in grain size, forming density, and micro chemical impurities.

Thus, the general purpose of ceramic processing is to provide a thermal stream, which should maximally (spatially and temporally) be determined by the particular thermodynamics, kinetics, mechanical behavior and technical arrangement of the particular ceramic sintering and densification. For all traditional kilns and furnaces this thermal stream acts from a flame torch and from a preheated ambient (refractory shell and air-gas mixture).

A real thermal stream inside a ceramic body depends on the thermal conductivity of the particular ceramic mass during its heating and sintering. Phase transformations begin after some critical temperature, and other processes and densification occur during all thermal processing. These cause a change in thermal conductivity in other parts of the ceramic body during heating.

Traditional firing technology eliminates all kinds of heterogeneity by providing an extra thermal flow. It decreases the thermal efficiency of the process, but creates the necessary quality of the ceramic item. According to the latest data, the maximum amount of thermal efficiency with heat associated with drying and firing processes is in the range of 50–70%, whereas the thermal efficiency of the heat which is employed directly for ceramic firing is 25–35%. If traditional technology is employed, the greater the size of the ceramic item, the greater the risk of ceramic cracking due to uneven heating development. To decrease this risk, the thermal processing (firing) time must be dramatically increased but that results in a decrease of thermal efficiency of up to 0.1–1% for large electrical porcelain items and vases. In some cases, in order to provide necessary densification, a combination of high pressure and high temperature—Hot Isostatic Pressing/Processing (HIP)—is used. However, that is a complicated and very costly technology.

Microwaves are invisible electromagnetic waves which are measured in megahertz, or millions of oscillations per second (MHZ). Microwave fields are reflected off metals, which they do not heat. Accordingly, metals are used for the walls of the microwave oven (furnace) cavities and microwave conduits.

The usual 60 Hz AC power is converted into DC power and this converted power is then placed across the special microwave tube (magnetron), which in turn converts the DC power into microwave energy at the particular voltage and frequency of 0.3 to 300 GHz (300 to 300,000 MHZ) with corresponding wavelengths ranging from 1 m to 1 mm. The microwave energy is transmitted to the microwave oven cavity through a metal wave-guide, whose width should be less than one wavelength and greater then one-half wavelength of the microwaves. The entire system, being electronic, has various control safety devices and feedback systems. To use the microwave furnace successfully it is necessary to take into account the danger of the invisible microwave field. That danger is a special concern in the industrial design of the conveyer kiln.

The Federal Communications Commission has directed that only 915 MHZ and 2450 MHZ be available for heating applications for home-practical purposes. However, it is possible to use other frequencies for special furnaces. Microwave oven magnetron power sources are now available at less than $100/kW.

There is considerable evidence that microwave energy can provide and accelerate ceramic densification and sintering reactions. The use of microwave energy to process a wide variety of ceramic materials offers many new and exciting opportunities in the processing of silicates, oxides, nitrides, and carbides by sintering formed (shaped) products from either green mass or purified powder. Sintering is accomplished by chemical reactions and/or diffusion at temperatures in excess of 500° C. with a maximum in excess of 1000° C.

Microwave heating has three special advantages over all other methods for heating all ceramic materials. The first is uniform and instantaneous microwave penetration and therefore uniform heating of the material body. It eliminates stresses and cracks that are caused by thermal gradients and that are a major problem of traditional external thermal processing of ceramics.

The second special advantage is a reverse heat-front propagation from center to surface resulting in a situation in which the material center temperature is higher than the surface temperature.

The third advantage of microwave ceramic processing is maximum energy efficiency because the ceramic body can absorb 95%–99% of the delivered microwave energy, and this energy can be converted into useful thermal-chemical energy. Generally, the efficiency of energy conversion depends on microwave frequency, power level, application type, cavity size, mode of energy delivery, mass volume of the sample, the number of treated ceramic physical-chemical characteristics, and sample consistency and preparation. All of these factors are theoretically adjustable, and an ideal microwave ceramic manufacturing system must be adaptive, flexible and versatile. It is necessary to determine experimentally what the appropriate adjustment should be for a particular ceramic product. The microwave field induces higher diffusion rates and substantially increases apparent activation energy for a sintering process as compared with conventional thermal processing. This is a result of changes in the matter-energy assumption. The specific influences of ceramic type, material composition, specimen preparation (initial grain size, porosity distribution, the presence of water and fluxes) on the densification and sintering behavior of several ceramics have been studied in a number of works.

Microwave energy is absorbed continuously within the material, and it increases the temperature of the material linearly up to a critical temperature (T-crit). After T-crit, which differs for different materials, the temperature rise is accelerated due to rapidly increased microwave absorption. Microwave ceramic thermal processing has special properties for heat delivery and thermal penetration. These properties cause a different dynamic and kinetics of the ceramic sintering and densification processes as well as other changes because of the consequences of particular physical-chemical interactions.

A theoretical consideration of the interaction between energy waves and ceramics has been provided using the classical approach of solid matter physics. The dielectric theory describes the power dissipation or energy absorption as well as the penetration depth of microwave in ceramic materials.

$$P_{ab}=(2pfe)(E^2/2)\tan d \quad (1)$$

where $P_{ab}$ (W/m$^3$) is the power dissipated, f is the frequency, e is the dielectric constant, E is the electric field strength, and tan d is the loss tangent for the dielectric.

$$D=1/(pfmd)^{1/2} \quad (2)$$

where D is the penetrated skin depth of the material when the electric field falls to 1/e or 37%, m is the magnetic permeability and d is the dielectric conductivity. These theoretical equations only estimate the processing of the physically and chemically homogeneous solid matter under stable phase conditions and do not consider the possibility of any physical-chemical change and transition during microwave ceramic processing.

The same and other physical parameters to describe the power absorbed (dissipated) by the sample:

$$P_{ab}=sE^2V=2pfe_oe_{\it{eff}}E^2V, \quad (3)$$

and the increase in temperature is:

$$DT=(sE^2)t/pc_p \quad (4)$$

where s is the conductivity, $e_o$ is the permeability of free space, $e_{\it{eff}}$ is the effective relative dielectric loss factor, p is the density, V is the volume, and $c_p$ is the specific heat (heat capacity) of the sample. The increase in temperature (DT) in time, t, depends on the density (p) of the sample.

An increase in the density (and the corresponding increase in thermal conductivity) of the sample results in reducing the heating rate. Thus, the two factors:—high compact density and high thermal conductivity—which limit or inhibit the wavefront propagation, and the reduced microwave heating rates (owing to the high density of the sample) provide control of the propagation of the densification. The rate of propagation of the wavefront can also be controlled by the incident power or frequency. Pulsing the incident power or frequency during the duty cycle gives precise control of the speed of microwave penetration and propagation of the densification. A microwave field couples more strongly to the regions of low sample density and low $e_{\it{eff}}$ and produces a uniformly densified sample. This uniform microwave heating, which travels from center to surface, results in an evaporation of burned ingredients and volatile gases and steam. These special characteristics prevent bloating and cracking of the ceramic body and permit the processing of large ceramic products and composites.

It is known that glass, plastic and ceramics are dielectric materials which have low thermal and electric conductivity and are permeable or transparent to microwaves. Physicists and materials scientists have considered these three materials as microwave-inert solid state matter which do not have any substantial ingredients or properties to absorb microwave. This is practically true for plain glass and plastic but plain ceramics can eventually be heated by microwave. Scientific publications did not explain this phenomenological difference since they usually considered only thermal and dielectric properties of glass, plastic and ceramics and did not combine them with the chemical properties of these materials.

In this invention, rapid and effective heating of ceramics by microwave can be partly explained by reference to a special branch of science—colloid chemistry. Colloid chemistry considers plain glass and plastic as one-phase solid substances which are hardened (solidified) from a molten state. With respect to colloid chemistry phenomena, ceramics should be a two or three phase colloid system consisting of a base solid phase with inclusions of a gas phase and (sometimes) a liquid phase since ceramics are mainly densified, consolidated and sintered from solid particles. Moreover, a ceramic colloid body (especially its surface area) is continuously open for interaction with ambient conditions.

The role of gas and liquid phases or hydrogen ions for ceramic-microwave interaction has never been previously considered. Moreover, artificial solid, gas and liquid additives to ceramics have never been theoretically considered or practically applied to induce or increase microwave ceramic processing though "sintering aids" or "susceptors" are well known in ceramic engineering.

Among recent publications there has been some consideration of the microwave-induced space charge polarization which induces diffusion of ceramic matter and ion transport as a practically important and direct physical-chemical resource of ceramic densification and sintering processes.

The total polarizability factor a of a dielectric material is a measure of the average dipole moment per unit of local field strength and can be represented by four phenomena:

$$a=a_e+a_i+a_o+a_s$$

where $a_e$ is the electronic, $a_i$ is the ionic, $a_o$ is the dipolar orientation, and $a_s$ is the space charge polarizability. Other dielectric materials may have one or more exclusive mechanisms. If one phenomenon acts especially strong, others may be negligible. But under some conditions all phenomena are negligible and the technological goal may be an enhancement of one phenomenon or an insertion of an additional ingredient with enlarged polarizability.

For example, when magnetic metal oxides are exposed to microwave energy, the magnetic poles of their micro particles are rotated. A similar excitation produces a dipole (neutral polar) molecule with spatially separated positive and negative electric charges. This is found in all liquids and water-containing materials because the resulting molecular friction generates heat. In these cases, the $a_o$ phenomenon acts especially strong, but it is not a major concern for most ceramics.

The $a_i$ and $a_e$ phenomena act as resistive heating of solid dielectric materials with relatively high dielectric resistivity and low dielectric constant. If the material has free electrons or electron pairs (such as carbon or silicon carbide), the $a_e$ phenomenon acts exclusively.

Those materials having an ionic content with a possibility of movement are heated exclusively according to the $a_i$ phenomenon. Two types of ionic microwave interaction may be noted. First, one which acts by ionic excitation from the impetus of charged atoms or radicals in electrolytic solutions (all water solutions are more or less electrolytes). A number of organic and inorganic colloid systems which contain a huge volume of water ions are known. Many ceramic materials, for example clay and kaolin, and minerals can be considered as colloids (two or three matter states) because they can contain water and hydrogen ions in alumina-silica lattice, in pores, and at the surface. In the heating range of 100°–160° C., absorbed water is removed when an ion dehydration process of the silicate lattice occurs in the range of 400°–800° C.

The second mechanism of ceramic ionic excitation results from the fact that most silicates and aluminates, which have a dielectric constant in the range of 5–15, have an anionic polarizability behavior. This is caused by the displacement of ions of opposite sign from their regular lattice sites under the influence of an applied field and also from the deformation of the electronic shells resulting from the relative displacement of the ions.

Ceramic electronic and ionic polarizability occurs in the range of $10^9$ to $10^{14}$ Hz when existing microwave-magnetron technical systems act in the range of $300 \times 10^9$ to $30 \times 10^{12}$ HZ. This means that ceramic electronic and ionic excitation by microwave energy takes place when an electrical circuit phase shift corresponds to a time lag between an applied current and induced ion and/or electron vibrations and/or transport, causing current loss, energy dissipation, and the heating of the ceramic material.

The microwave induced effect of ion material transport due to an electric field is an irreversible pushing effect has been theoretically considered and experimentally proved. It was also attributed to the difference between the time scale of thermally activated atomic jump processes ($10^{-13}$ s) and the applied microwave frequency ($10^{-9}$ s). Also, ". . . it has been concluded, that the enhanced densification upon microwave sintering would result from a superposition of thermally activated transport phenomena with an electrical potential . . . In conventional sintering, grain boundary mobility and grain growth, as well as impurity segregation, are controlled by this space charge." Willert-Porada, M., "The Role of Space Charge for Microwave Sintering of Oxides," *Microwaves: Theory and Application in Material Processing III.* Ceramic Transactions; The Am. Cer. Soc., Westerville, Ohio. 1995, 192–203.

This means that microwave induced space charge polarization $a_s$ can affect the ceramic grain densification process, which is the transport of uncharged vacancies from the pore region through the neck region to the exterior of the grain. This process may take place in a medium temperature range, where the space charge has a significant value.

This explains a substantial decrease (100–200° C. and more) in the range of the microwave sintering temperature of ceramics in comparison with traditional external heating technique. Obviously, space charge polarization may affect in the presence of micro-grain and micro-pore structure which is usual for other clay, kaolin, mineral and partly sintered/densified ceramic materials; whereas glass does not have this structure and therefore cannot be heated by microwave.

FIG. 7 is a plot of the heat capacity of perlite where curve 1 refers to the original mineral material; curve 2 pertains to the same perlite after annealing at 1000° C.; and curve 3 refers to the bloated perlite after shock heating (special thermal processing) of the initial mineral.

Curves 1 and 3 reveal the change in heat capacity as various hydrogen forms are removed from the material samples in a temperature range from 323 K to 1350 K. For curve 1, the major effect is exothermic, which reflects the presence of a particular combination of 1–4, 6 and 7 hydrogen forms (Table 3). Curve 2, which shows only a gradual change in heat capacity with temperature, indicates that the material does not contain hydrogen. Shock heating of perlite causes bloating of the mineral material. Obviously, this material easily takes up water and hydration forms from the surrounding space (ambience) because of a huge porous volume and surface area.

Hydrogen form contents could be increased by using autoclave steam treatment as shown by sample 3. Curve 3 of FIG. 7 shows the dip in heat capacity in the range of temperatures from about 753 K to 1073 K, which results from the endothermic effect of the OH⁻ ions.

Molecules, crystal, capillary, and pore absorbed hydrogen and water can be simultaneously present in ceramics up to 1200–1300 K. This is indicated by curves 1 and 3 of FIG. 7 and is illustrated by Table 3. Obviously, there are different bonds between hydrogen forms and ceramics and these bonds are stronger at the surface of the pore, cavern or canal, which corresponds with the particular ceramic lattice. Various forms of hydrogen have been examined by infrared spectroscopy and optical light refraction methods, and, significantly, all these forms could be ions or a source for ions if a heating process is provided.

A number of minerals and ceramics have an alumina-silicate type lattice as typified by silica, feldspar and pegmatite, which are usual for red clay. This type of lattice permits the formation of a large volume of micro caverns and canals which can capture and take up water molecules and hydrogen ions.

If the likelihood of lattice hydrogen is a property of silicate ceramics, a surface water-hydrogen absorption is possible for all types of ceramics. The surface area of the ceramic bulk-piece materials—and especially fly ash—is huge. For example, on the basis of gas absorption measurement, it was shown that the surface area of bloated perlite powder is in the range of 2.3 to 5.2 m²/gram. This surface area is available for the capture of various forms of hydrogen. The equilibrium concentration of various hydrogen forms can attain about 3% of the material weight.

TABLE 4

Possible Hydration Forms and Their Thermodynamic Characteristics

| No. of hydration form | Formulas of ion compounds | State | Entropy, $S_{298}^0$ (cal/degree × mole) |
| --- | --- | --- | --- |
| 1 | H | Gas | 27.39 |
| 2 | $H_2$ | Gas | 31.21 |
| 3 | $H^+$ | Solution | 0 |
| 4 | OH | Gas | 43.89 |
| 5 | $OH^-$ | Solution | −2.52 |
| 6 | $H_2O$ | Gas | 45.11 |
| 7 | $H_2O$ | Molecules in a diluted solution | 16.72 |

The major part of the weight of the hydrogen forms is represented by $H_2O$ molecules, which are "low-temperature or moisture and capillary water" because these water molecules can be removed at from 100° C. to 350° C. (No. 6 and No. 7 forms in Table 4).

One $\mu m^2$ of the alumina-silica or silica lattice can take eight OH⁻ groups. One gram of the material with an inner surface area of 5.2 m² can absorb $8 \times 5.2 \times 10^{18}$ or $4.2 \times 10^{19}$ OH⁻ groups. This is equivalent to $7 \times 10^6$ OH⁻ g-mole for 1 gram of the material, or approximately 0.1% of the weight. This shows that a huge quantity of OH⁻ groups can be captured and be present in ceramic materials. A second important conclusion would be that the other hydrogen forms are also available for absorption in the quantity of 3−0.1=2.9 weight percent.

When ceramic powder and formed items are heated by microwaves, the heating occurs substantially faster and requires 10–30 times less energy expenditure than that required for a bulk solid piece. The surface area of ceramic powder depends on particle size and material property. This has significant practical importance, because it is not difficult to prepare the appropriate size particles or powder, and thereby facilitate the hydrogen absorption process.

During autoclave steam treatment, it is possible to produce other hydrogen forms, and the maximum quantity of the absorbed hydrogen forms could be up to 70–80% of the "water" form content of the corresponding natural raw material. That indicates that the autoclave treatment can be an instrument for an artificial hydration of the ceramic materials.

As is shown by FIGS. 7 and 8 and as explained by Table 3, steam pressure and time of the treatment influence the quantity and types of particular hydrogen form that may be inserted in silicate material. However, FIG. 8 shows the total quantity of hydrogen forms inserted by the autoclave steam. FIG. 8 identifies maximum conditions for steam autoclave treatment of ceramic grain or powder materials. It is preferably conducted at up to about 2.45 GPa steam pressure (approximately 21 atmospheres) during a maximum of about 12 hours.

The hydrogen forms function as microwave susceptors which respond to microwaves. Hydrogen forms instantaneously generate heat which increase ceramic temperature up to the critical point when certain types of ceramic material, for example alumina ceramics, starts their response employing additional coupling mechanisms.

It is important that hydrogen forms are not associated with any impurities, and their really small quantity cannot impair the ceramic body properties, partly diluting the materials of the ceramic body and partly vaporizing.

This method makes it possible to precisely furnish a thermal-time-schedule of the process and to obtain a uniformity of the thermal field which provides a gentle thermal impact for each surface point of a ceramic component. In order to obtain ceramic quality and decrease energy, thermal aggregates (drier and kiln) are consumption equipped with two hydraulic circulation systems.

Each circulation system is equipped with a small blow fan and a set of jet-nozzles for free-running gas/air mixture or air. The first circulation system provides gas-air delivery from cooling zone to the heating and firing zones, and the second circulation system provides air delivery from outside space to the cooling zone of the kiln.

Additionally, the first circulation system delivers hot gas-air mixture to the drier and then a surplus of the hot gas-air mixture is injected to the chimney.

A part of the gas-air injection process within the thermal aggregate is provided by vertical jet-nozzles which are positioned along the thermal aggregate. The vertical direction of the nozzles maintain vertical uniformity of the thermal treatment of the ceramic product.

To obtain uniform and gentle convective impact of the hot air on the ceramic product surface, a ratio of the length of the air current stream to the nozzle diameter is about 100–250.

The injection jet nozzles provide mixing and circulation of the thermal aggregate inner atmosphere. The mixing ratio is one volume part of the gas to the following parts of air:
  a. 40–80 for drying process when low temperature gas is delivered to the dryer from the heating zone of the kiln or
  b. 60–100 for the heating and firing processes when high temperature gases from the cooling zone of the kiln are delivered to the heating and sintering zones of the same kiln.

To prevent an output of the kiln gases to the shop space, some of the nozzles are directed horizontally to the product entrance of the kiln. This provides gas-air horizontal flow with a necessary ejection of the outside air which causes a lower gas-air pressure within kiln canal compared to regular atmosphere pressure.

Firing of large-scale thick-wall ceramic items, such as vessels and lids of ceramic containers for nuclear and hazardous waste, comprises a setting of a ceramic item on a car-platform or on horizontal rollers for the periodical or conveyer movement consequently into a compartment chamber or through a tunnel canal. The method of ceramic firing and tunnel kiln construction includes a special construction of the kiln car—FIG. 6. This car provides movement of the ceramic item in a vertical position within the tunnel kiln.

Other utilities for the large scale, thick-walled ceramic products of the invention are:
  (i) Large ceramic housing and building construction modules, which are suitable for crane assembly and can provide perfect hygienic properties for a room, as a substitute for traditional masonry ceramic brick and hygienically worse materials, such as vinyl siding and concrete blocks;
  (ii) Large ceramic road-sidewalk (pavement) cover plates which are suitable for immediate crane installation to accelerate road construction works;
  (iii) Large ceramic gas-tank plates and other ceramic construction with the best wear, chemical and water corrosion resistance;
  (iv) Ceramic composite materials with low specific gravity, nuclear and electrical insulation properties, radar invisibility and transparency and armor properties for automotive, air-space and defense industries;
  (v) Large ceramic products for electrical insulators, chemical and foot-processor vessels;
  (vi) Joining, sealing, coating, and covering of ceramic items;
  (vii) The substitution of inexpensive and rapid microwave processing in place of extremely expensive and complicated hot isostactic pressing (HIP) of $B_4C$, BN, SiC and other oxide and non-oxide ceramics.

Additionally, (i) and (ii) technologies offer significant potential for the utilization of enormous quantities of ash, slag and cinder generated by metallurgical and electrical power plants and by garbage incineration industries.

The foregoing specification and drawings have thus described and illustrated a novel microwave-assisted process for producing large-sized, thick-walled ceramic products, which fulfills all the objects and advantages sought therefor. Many changes, modifications, variations and other uses and applications of the subject invention, however, become apparent to those skilled in the art after considering this specification which discloses the preferred embodiments thereof. All such changes, modifications, variations and other uses and applications which do not depart from the spirit and scope of the invention are deemed to be covered by the invention, which is to be limited only by the claims which follow.

What is claimed is:

1. A process for the preparation of ceramic articles having a thickness of at least about 2.5 cm, which comprises:
  (a) selecting a basic particulate ceramic composition from the group consisting of kaolin, silicate materials, red clay, mullite, alumina, magnesium oxide, magnesium aluminum spinel, nitrides and carbides, and mixtures thereof,
  (b) autoclaving the ceramic composition to increase its hydrogen form contents to a concentration that serves to increase the composition's absorption of microwave energy during subsequent heating of the ceramic article,
  (c) forming the ceramic composition into the desired shape, and (d) subjecting the composition so shaped to microwave energy to internally heat and thereby dry and sinter the composition.

2. The process as claimed in claim 1, wherein the ceramic articles have a thickness of at least about 5 cm.

3. The process as claimed in claim 1, wherein the particle sizes of the basic particulate ceramic composition range from about 2 nm to about 2 mm.

4. The process as claimed in claim 1, wherein the ceramic mass is subjected to a steam autoclave treatment at a steam pressure of up to about 21 atmospheres for a period of time sufficient to introduce hydrogen forms into the ceramic composition.

5. The process as claimed in claim 4, wherein the mass is subjected to a steam autoclave treatment at a steam pressure of up to about 21 atmospheres for a period of time sufficient to introduce hydrogen forms into the ceramic composition in an amount that serves to increase the absorption of microwave energy during the heating of the ceramic article up to about 800 C.

6. The process as claimed in claim 1, wherein there is present in the basic particulate ceramic composition borosilicate glass, chromium trioxide, plastificators and sintering aids, or mixtures thereof as an additive.

7. The process as claimed in claim 6, wherein the additive is present in a total amount up to about 20 weight percent.

8. The process as claimed in claim 1, wherein the microwave energy is provided at one or more frequencies in the range of about 600 MHZ to about 6000 MHZ.

9. The process as claimed in claim 8, wherein the microwave energy is provided at one or more frequencies in the range of about 700 MHZ to about 4000 MHZ.

10. The process as claimed in claim 9, wherein the microwave energy is provided at a frequency of about 915 MHZ or about 2450 MHZ.

11. The process as claimed in claim 9, wherein the microwave energy is provided at both about 915 MHZ and about 2450 MHZ.

12. The process as claimed in claim 1, wherein the power of the microwave energy to be used is determined by the properties of the mass of the ceramic composition and body volume of the ceramic article.

13. The process as claimed in claim 1, wherein external heat applied by means of electrical resistance or gas- or oil-fired heating is additionally used.

14. The process as claimed in claim 1, wherein the shaped composition from step (c) is transported through step (d) in a continuous manner.

15. The process as claimed in claim 14, wherein the shaped composition from step (c) is transported through step (d) in a vertical position by means of a rail car system.

16. The process as claimed in claim 15, wherein the shaped composition from step (c) is generally in the form of a cylinder or an egg-shape and is rotated about its axis in step (d).

17. The process as claimed in claim 1, wherein:
(a) a heat fan blows outside air into a cooling zone through injection nozzles in the ceiling of a tunnel kiln, some of which are directed downward and some of which are directed to provide air flow countercurrent to the travel direction of the ceramic articles through the kiln,
(b) a second fan takes air heated from the heated and fried ceramic articles in the cooling zone and delivers it to the heating and firing zones of the kiln and thereafter to a dryer for the drying of a green ceramic article.

18. The process as claimed in claim 17, wherein to obtain uniform and gentle convective impact of the hot air on the ceramic product surface, a ratio of the length of the air current stream to the nozzle diameter is about 100–250.

19. The process as claimed in claim 17, wherein the injection jet nozzles provide mixing and circulation of the thermal aggregate inner atmosphere with a mixing ratio of one volume part of gas to the following parts of air:
(a) 40–80 for drying process when low temperature gas is delivered to the dryer from the heating zone of the kiln or
(b) 60–100 for the heating and firing processes when high temperature gases from the cooling zone of the kiln are delivered to the heating and sintering zones of the same kiln.

20. A process for the preparation of ceramic articles having a thickness of at least about 2.5 cm, which comprises:
(a) batching of additives,
(b) batching of a fine grain ceramic powder composition,
(c) batching of a coarse grain ceramic composition,
(d) the fine grain ceramic powder composition and the coarse grain ceramic composition being a basic particulate ceramic composition selected from the group consisting of kaolin, red clay, mullite, alumina, magnesium oxide, magnesium aluminum spinel, and mixtures thereof,
(e) mixing the additives with water or a polar liquid,
(f) mass mixing of the fine grain ceramic powder composition and the coarse grain ceramic composition,
(g) steam autoclaving the composition from step (f) to increase its hydrogen form contents to a concentration that serves to increase the composition's absorption of microwave energy during heating of the ceramic article,
(h) mixing the mixtures from steps (e) and (g) to produce a ceramic mass,
(i) forming the ceramic mass into the shape of the article desired,
(j) predrying the shaped mass to form a green ceramic body,
(k) drying the green body with microwave energy, and
(l) frying the dried green body with microwave energy to internally heat and thereby sinter the composition.

21. The process as claimed in claim 20, wherein the ceramic articles have a thickness of at least about 5 cm.

22. The process as claimed in claim 20, wherein the particle sizes of the basic particulate ceramic composition range from about 2 nm to about 2 mm.

23. The process as claimed in claim 20, wherein there are used coarse grain particles which comprise about 63–67% of a grain fraction composition and fine grain fraction comprise about 23–25% of the grain fraction composition, the remaining portion of the grain fraction composition being comprised of nanophase or kaolin particles having a size which is less than about 60 nm.

24. The process as claimed in claim 20, wherein the mass is subjected to a steam autoclave treatment at a steam pressure of up to about 21 atmospheres for a period of time sufficient to introduce hydrogen forms into the ceramic composition in an amount that serves to increase the absorption of microwave energy during the heating of the ceramic article up to about 800 C.

25. The process as claimed in claim 20, wherein the amount of water or polar liquid is sufficient to mix, plastificate and prepare a homogeneous mass and yet not so much as to adversely increase the drying time.

26. The process as claimed in claim 25, wherein the amount of water or polar liquid is at least about 5 weight percent.

27. The process as claimed in claim 25, wherein the amount of water or polar liquid ranges from about 5 to about 10 weight percent.

28. The process as claimed in claim 20, wherein ceramic fibers or whiskers are also present in the ceramic composition.

29. The process as claimed in claim 28, wherein the ceramic fibers or whiskers are formed from boron, alumina, mullite, boron nitride or silicon carbide.

30. The process as claimed in claim 20, wherein the drying of the shaped composition is conducted by means of microwave energy supplied to internally heat and thereby dry the composition with external heat applied by means of electrical resistance or gas- or oil-fired heating.

31. The process as claimed in claim 20, wherein the firing of the shaped composition is conducted by means of microwave energy supplied to internally heat and thereby sinter the composition with external heat applied by means of electrical resistance or gas- or oil-fired heating.

32. The process as claimed in claim 20, wherein the ceramic articles are containers formed by extrusion of the vessels.

33. The process as claimed in claim 20, wherein the ceramic articles are lids for containers formed by extrusion.

34. The process as claimed in claim 20, wherein the ceramic articles are containers formed by vibrocompacting of egg-shaped vessels.

35. The process as claimed in claim 20, wherein ceramic articles are lids for containers formed by vibrocompacting.

36. The process as claimed in claim 20, wherein the microwave energy is provided at one or more frequencies in the range of about 600 MHZ to about 6000 MHZ.

37. The process as claimed in claim 36, wherein the microwave energy is provided at one or more frequencies in the range of about 700 MHZ to about 4000 MHZ.

38. The process as claimed in claim 37, wherein the microwave energy is provided at a frequency of about 915 MHZ or about 2450 MHZ.

39. The process as claimed in claim 37, wherein the microwave energy is provided at both about 915 MHZ and about 2450 MHZ.

40. The process as claimed in claim 20, wherein the green ceramic body is machined to more precise dimensions of its edge.

41. The process as claimed in claim 20, wherein the green body is dried and fired by means of a combination of microwaves and heating from either gas- or oil-fired or electric heaters.

42. The process as claimed in claim 20, wherein the shaped composition from step (e) is transported through step (i) in a continuous manner.

43. The process as claimed in claim 20, wherein the shaped composition from step (e) is transported through step (i) by means of a roller conveyor or a rail car system.

44. The process as claimed in claim 20, wherein the shaped composition from step (i) is in the form of a cylinder or an egg-shape and is rotated about its axis.

45. The process as claimed in claim 20, wherein:
   (a) a heat fan blows outside air into a cooling zone through injection nozzles in the ceiling of a tunnel kiln, some of which are directed downward and some of which are directed to provide air flow countercurrent to the travel direction of the ceramic articles through the kiln,
   (b) a second fan takes air heated from the heated and fried ceramic articles in the cooling zone and delivers it to the heating and firing zones of the kiln and thereafter to a dryer for the drying of a green ceramic article.

46. The process as claimed in claim 20, wherein to obtain uniform and gentle convective impact of the hot air on the ceramic product surface, a ratio of the length of the air current stream to the nozzle diameter is about 100–250.

47. The process as claimed in claim 20, wherein the injection jet nozzles provide mixing and circulation of the thermal aggregate inner atmosphere with a mixing ratio of one volume part of gas to the following parts of air:
   a. 40–80 for drying process when low temperature gas is delivered to the dryer from the heating zone of the kiln or
   b. 60–100 for the heating and firing processes when high temperature gases from the cooling zone of the kiln are delivered to the heating and sintering zones of the same kiln.

* * * * *